United States Patent
Bunt et al.

(10) Patent No.: US 6,352,524 B1
(45) Date of Patent: Mar. 5, 2002

(54) ACTIVE DELIVERY DEVICE WITH REDUCED PASSIVE DELIVERY

(75) Inventors: Craig Robert Bunt; Michael John Rathbone; Shane Burggraaf, all of Hamilton (NZ)

(73) Assignee: Interag, Hamilton (NZ)

( * ) Notice: Subject to any disclaimer, the term of this patent is extended or adjusted under 35 U.S.C. 154(b) by 0 days.

(21) Appl. No.: 09/207,514

(22) Filed: Dec. 9, 1998

Related U.S. Application Data

(63) Continuation-in-part of application No. PCT/NZ98/00011, filed on Feb. 2, 1998.

(51) Int. Cl.⁷ ............................................. A61M 31/00
(52) U.S. Cl. ..................... 604/285; 123/130; 606/119
(58) Field of Search .................... 606/119; 604/514, 604/515, 518, 93.01, 132, 140–148; 128/831, 832

(56) References Cited

U.S. PATENT DOCUMENTS

| | | | | |
|---|---|---|---|---|
| 3,993,057 A | * | 11/1976 | Ramwell | 128/833 |
| 4,582,052 A | * | 4/1986 | Dunn et al. | 128/839 |
| 4,678,463 A | * | 7/1987 | Millar | 604/285 |
| 4,969,874 A | | 11/1990 | Michel et al. | 604/140 |
| 5,062,834 A | | 11/1991 | Gross et al. | 604/143 |
| 5,090,963 A | | 2/1992 | Gross et al. | 604/132 |
| 5,156,591 A | | 10/1992 | Gross et al. | 604/20 |
| 5,318,557 A | | 6/1994 | Gross | 604/891.1 |
| 5,354,264 A | | 10/1994 | Bae et al. | 604/21 |
| 5,492,534 A | | 2/1996 | Athayde et al. | 604/141 |
| 5,527,288 A | | 6/1996 | Gross et al. | 604/140 |
| 5,951,538 A | * | 9/1999 | Joshi et al. | 604/500 |
| 6,186,997 B1 | * | 2/2001 | Gabbard et al. | 604/408 |

FOREIGN PATENT DOCUMENTS

| | | |
|---|---|---|
| EP | 0385915 | 9/1990 |
| GB | 2154875 | 9/1985 |
| NZ | 207341 | 2/1988 |
| WO | WO90/02580 | 3/1990 |
| WO | WO94/01165 | 1/1994 |
| WO | WO96/04953 | 2/1996 |
| WO | WO96/29025 | 9/1996 |
| WO | WO97/40776 | 11/1997 |
| WO | WO98/53758 | 12/1998 |

* cited by examiner

*Primary Examiner*—Kim M. Lewis
(74) *Attorney, Agent, or Firm*—Jacobson Holman, PLLC

(57) ABSTRACT

A delivery device having a reservoir of variable volume having an outlet through which an included vehicle can be expressed in a liquid form as the volume of the reservoir is actively reduced. There is a tube providing a conduit to the outlet from the reservoir of such length and cross-section as to favor active release over passive release which has the effect of enabling a more positive control of the dispensing of the vehicle. Such a device has diverse applications.

28 Claims, 20 Drawing Sheets

FIG. 6A
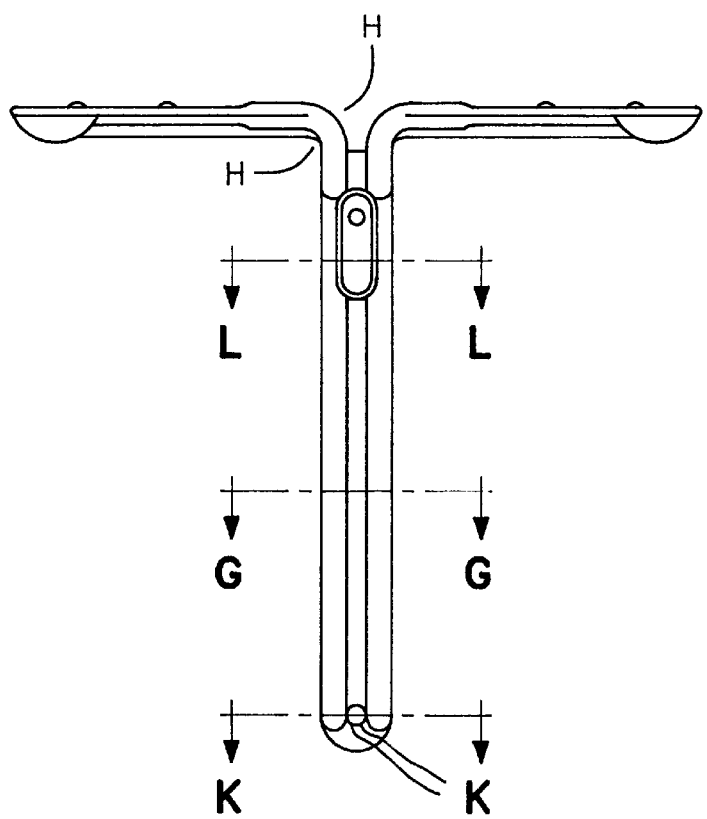
FIG. 6B
FIG. 6C
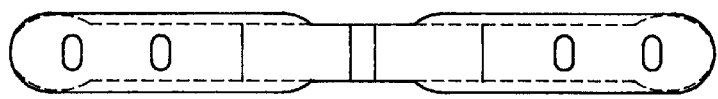
FIG. 6D
FIG. 6E  FIG. 6F  FIG. 6G
 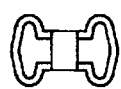 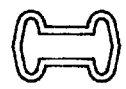
FIG. 6H  FIG. 6I
 

Plasma progesterone levels for individual ovariectomised cows with CIDR-B devices inserted for 10 days.

Plasma progesterone levels for individual ovariectomised cows with SMARTT/™ IBD inserted for 12 days.

This figure shows the in vitro release rate of vehicle from a device using two different currents (250 mA (□) and 500mA (■)) and therefore rates of gas production. Errorbars are standard error mean (n=3)

This figure shows the plasma progesterone levels obtained using 2 devices with a gas production and control unit (■) or one without a gas and control production unit (x). Also shown is the plasma progesterone concentration for a conventional CIDR-B (□, n=4).

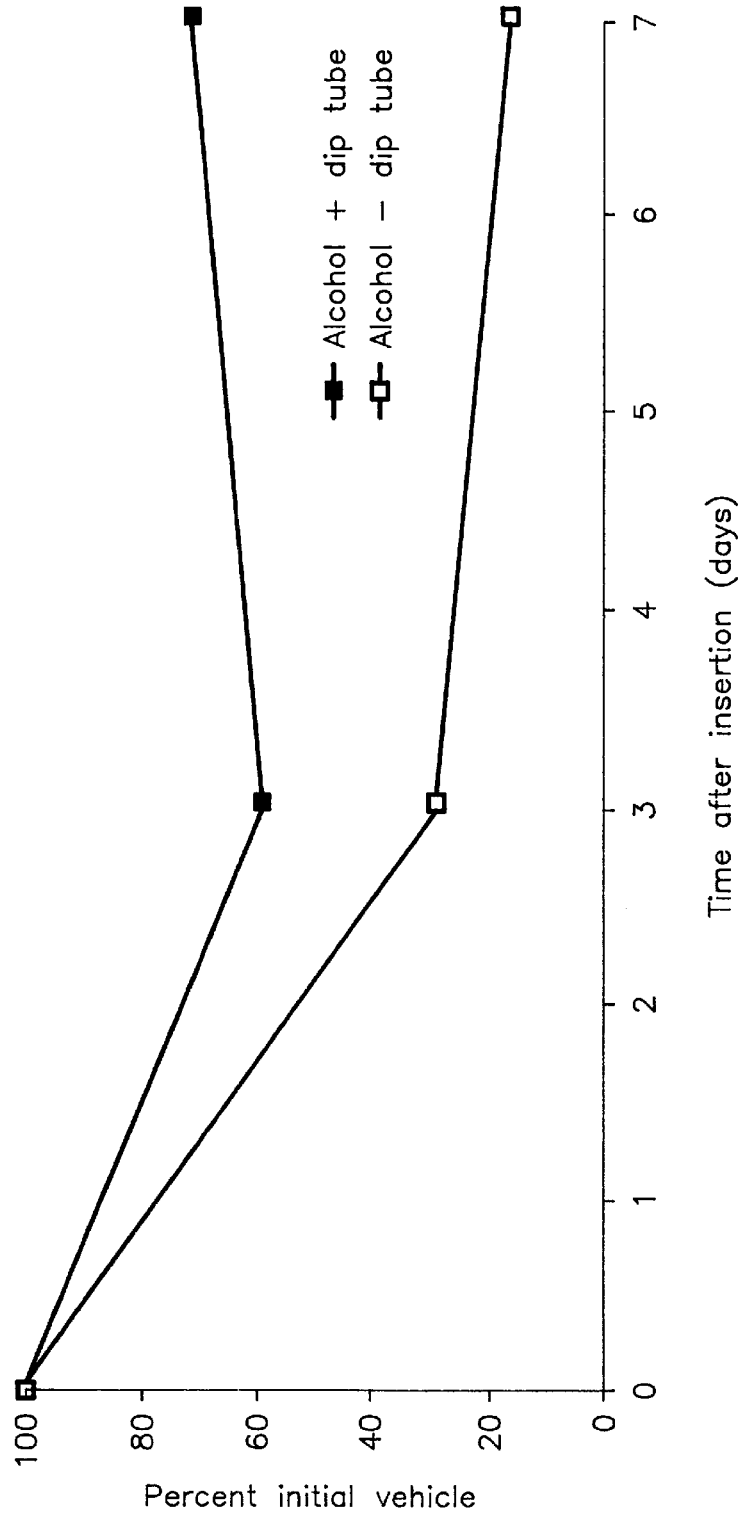

Figure (16A) circuit diagram for the controlled production of gas by a hydrogel electrolytic cell.

Figure (16B) circuit diagram for the controlled production of gas by a hydrogel electrolytic cell.

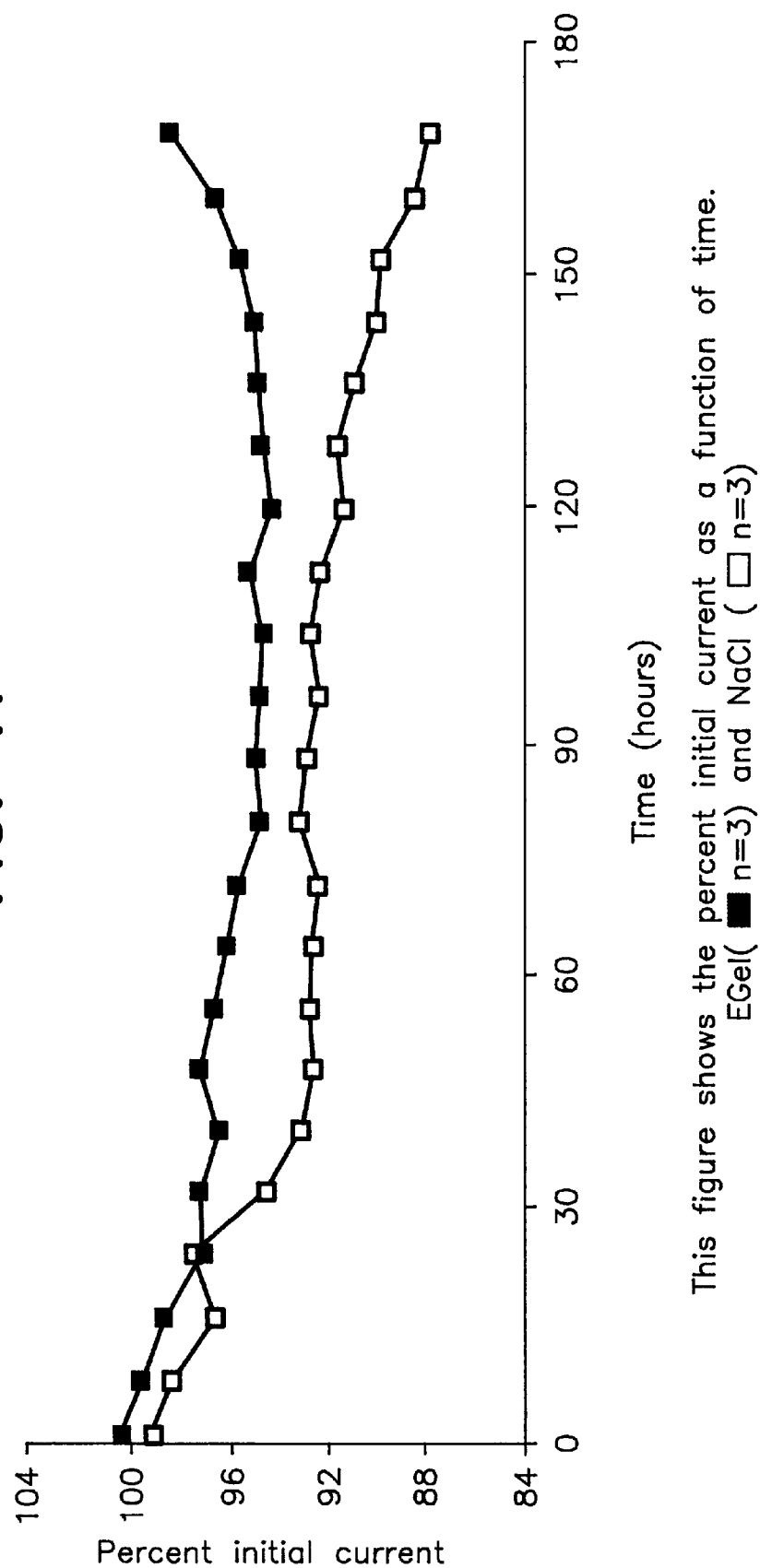

ACTIVE DELIVERY DEVICE WITH REDUCED PASSIVE DELIVERY

This application is a continuation-in-part of PCT application No. PCT/NZ98/00011, filed Feb. 2, 1998.

The present invention relates to active delivery devices and related procedures.

More particularly the invention relates to devices or inserts (hereafter "devices") capable of delivering a substance from the device into a surrounding environment whatever that may be. Such delivery will be as a fluid from a storage reservoir for such fluid or its precursor.

Unlike passive diffusion devices of this type the present invention is directed to a device which can achieve an active expression of the fluid from a storage reservoir for such fluid or its precursor and preferably with control of the continuous or intermittent reduction of the volume of the reservoir which achieves the active expression and preferably with a low passive release incidence to any active release incidence and also preferably with a low passive release incidence during any period of no active release.

The environment of any such release may vary.

Such environments include body cavities, plant beds, loci of pest movement, liquid surrounds (eg fish tanks), etc.

The reason for the preferred characteristics will now be described by reference to non-restrictive examples of such use.

As a first example the invention may relate to active delivery devices locatable in a body cavity of an animal to actively release a substance (eg. useful by intra-vagina insertion of synchronising the oestrus of animal or by intraruminal delivery of releasing desired agents into a ruminant).

When one considers the mating of animals, it is useful for farmers to synchronise the oestrus of animals whether they be cattle beasts (whether for dairy or beef purposes) sheep, goats, horses, or the like where artificial insemination is practised. By way of example, in relation to cattle beasts, in a normal 365 day year 282 days on average is taken up of the year with the gestation period itself. With approximately 30 days to recover after delivery of its progeny each cow therefore has an average of only two and a half cycles if there is to be a timely management of the herd. Thus it is important over that remaining period of less than 53 days to ensure each cow in a herd becomes pregnant.

The traditional method of mating dairy cows with bulls is now largely superseded by the use of artificial insemination procedures which offers the prospect of rapid herd improvements although bulls are still presented to the herd frequently to catch those animals that have not conceived by the artificial insemination procedure should they comes into oestrus within a designated time.

There is therefore a great advantage attached to bringing such herd animals into oestrus simultaneously so as to make it easier to ensure effective usage of the artificial insemination procedure and subsequently to enable still within the "window" a further prospect of artificial insemination of those animals synchronistically brought to oestrus that have not already conceived.

BACKGROUND OF THE INVENTION

Various means of achieving such a management of the synchronisation of the coming into oestrus of cows (whether heifers or lactating cows) and even sheep and goats has been disclosed in the art which includes the livestock improvement publication of this company (1995 edition) made available to interested parties by this company trading as INTERAG™ in respect of its intra vaginal Eazi-Breed™ CIDR® product line.

The disclosures in the aforementioned publication, the full contents of which are here included by way of reference, ensures to date the best procedure applicable (at least to New Zealand herds) of cattle beasts to ensure a timely conception of a herd without a significant downgrading of the fecundity of the herd.

As used herein the term "synchronise" or the derivatives thereof in respect of the onset of oestrus of an animal is not restricted to exact synchrony but rather relates to a period of time usually measured in days over which the synchrony occurs.

Initial attempts using intra vaginal devices from which progesterone could be leached simply had the effect of preventing oestrus until after they were withdrawn thereby deriving some synchrony in the onset of oestrus thereafter during a period when a heifer or lactating cow is able to cycle. This lead to a three day spread in the synchrony after a 12 to 15 day insertion of the intra vaginal progesterone containing device.

Subsequent efforts to confine the period of the synchrony lead to such a progesterone containing intra vaginal device being inserted shortly after, simultaneously with or shortly before the administration (usually intra vaginally) of an oestradiol. For instance the use of a CIDR® intra vaginal device as referred to the aforementioned publication simultaneously with a capsule containing ten milligrams of oestradiol and the retention of the CIDR® intra vaginal device in the animal for ten days led shortly thereafter to a three day synchrony onset of oestrus period.

More recently that last mentioned procedure has been refined for heifers to provide a two day period of synchrony with an 80% of the herd onset of oestrus within the first day. In this refined procedure at about day 6 of the 10 day insertion period a prostaglandin is injected.

The aforementioned procedures are now described in the art. Also described in the art are insemination procedures. It is also known to use substantial repeats of the procedure within the available cycling period referred to so that there is at least one additional prospect of conception by artificial breeding within an appropriate economic window.

With all such procedures however the longer the period of the presence of the progesterone containing intra vaginal device in an animal (about 15 days is the optimum for tightness of the synchronisation) there is a corresponding diminishment in the fertility of individual animals in the herd owing to the effect over time on the follicle development to the fertilisable egg stage. The use of the oestradiol changes follicle growth pattern. Hence with its use an optimisation of the fecundity prospects for the herd can be achieved by better balancing the tightness of the synchronisation (with longer insertion) against the loss of fertility (with longer insertion).

A cost factor arises in the adoption of such procedures as a farmer is faced with the costs of the intra vaginal progesterone containing device as well as the use of the oestradiol and/or prostaglandin materials additionally used. This ignores also the economic cost of the artificial breeding materials themselves.

The intra vaginal progesterone containing devices hitherto used in New Zealand and to a large extent elsewhere are typified by the CIDR® product of this company depicted hereinafter in FIGS. 1 and 2 being a variable geometry device for vaginal insertion and retention which comprises a structural frame of a metal or appropriate plastics material (eg. nylon) encased in a progesterone impregnated plastics material (eg. silicone) from which the material can leach in the vaginal environment and from which it can be timely withdrawn by appropriate means (eg; a string, tail or a tool) to allow the animal to progress into oestrous shortly after the removal. Reference should be made to New Zealand Patent Specification No. 207341 (U.S. Pat. No. 4,678,463). Hereinafter the aforementioned device will be referred to by its registered trademark CIDR®.

The prior art CIDR™ devices of this company are intra vaginal passive delivery systems to be used in cattle for the control of oestus. Two major uses are in the treatment of anoestrus and synchrony. Other uses include its role in embryo transfer and treatment of cystic ovaries.

Another product available in the market place of this kind is another variable geometry device and such a device is depicted hereinafter in FIG. 3. Such a device is a helical coil capable of being helically tightened and which is retainable in its helical form in the animals vagina. The device includes a withdrawal cord and carries a gelatine capsule which includes oestradiol so that there can be co-administration of the progesterone to be released over a protracted period and the oestradiol which is to be released at a different rate. Such a device includes a progesterone impregnated plastics matrix about a helical spine. Such a device is available from Sanofi Animal Health Limited, PO Box 209, Rhodes Way, Watford, Herts, WD2 4QE, England under its registered trademark PRID®.

Species specific enhancements to better ensure retention of devices abound. See for instance New Zealand Patent Specification No.286984/299060 (PCT/NZ98/00064) that is relevant to pigs.

The aforementioned CIDR® and PRID® devices are manufactured in large volumes with the most expensive material being the progesterone active ingredient. Thus small reductions in the progesterone inclusion in such the devices will provide an economic advantage to a producer and to a farmer.

The CIDR® prior art device of this company has been marketed with a silicone plastics matrix about its spine which contains about 1.9 grams of progesterone (USP) which drops to 1.25 grams still retained in the silicone matrix if the device is withdrawn after only seven days in order to maximise fertility. The same device drops to 1.00 grams of progesterone if it is not withdrawn until after 15 days which is the optimum time for ensuring maximum synchrony.

The PRID® coil intra vaginal device contains at the outset 1.55 grams of progesterone which reduces down to 0.55 grams after 7 days and down to 0.86 grams after 15 days. The leach rate from the PRID® product may be affected in part by the inclusion of inorganic materials in the silicone plastics material such as calcium carbonate. The CIDR® silicone matrix for the progesterone is largely free of any such inclusions.

Our New Zealand Patent Specification No. 286492 (PCT/NZ97/00052 or WO97/40776) discloses a passive delivery device of the CIDR™ type having advantages insofar as reducing the progesterone content is concerned but without any diminution of the delivery. In this respect please see FIG. 13 which is a plot of the plasma progesterone levels for individual ovariectomised cows with this particular intra vaginal passive delivery device (CIDR-B™) against time. While the individual profiles of individual animals varies having regard to the nature of the animal, eg; its vaginal liquids etc. a general trend is evident, viz, a rapid release upon device insertion to rapidly elevate progesterone plasma levels above 2 ng/mL and to maintain a progesterone plasma level above 2 ng/mL until device removal whereupon the progesterone plasma level rapidly drops.

Therefore a programme of passive delivery utilising the CIDR-B™ with a silicone elastomer containing progesterone moulded over a T shape nylon spine and a CIDRIOL™ capsule which contains oestradiol benzoate and is administered attached to the CIDR-B™ can act to ensure that a fresh follicle is present from the onset of progesterone delivery by the CIDR-B™ device. The length of insertion of the CIDR-B™ device varies but a period as short as five days can now be used. Within 24–48 hours after removal of the device the animal will enter oestrus thereby allowing the predetermined timing of insemination.

Active delivery devices have been used for the delivery of active ingredients into the bodies of mammals (whether for therapeutic purposes with a human or in order to achieve a therapeutic or some other advantageous effect in a non human mammal).

For example, PCT/US89/03705 (published as WO 90/02580) to Brown University Research Foundation discloses an implantable delivery system for biological factors. The disclosure envisages in some instances the use of a preprogrammed micro-processor to control a pumping system responsible, when activated, of actively delivering a desired therapeutic, biologically-active factor, (such as a drug) into the target region into which the implantable device has been inserted.

In September 1996 Plade Holdings Limited launched an active delivery device into the New Zealand market for delivery of active ingredients via the vaginal tract. The device was launched as the SMARTT1™ Intelligent Breeding Device. It included a micro-processor chip programmed to deliver three different active ingredients—progesterone, oestradiol benzoate and clonprostenol sodium at various times and durations during a 12 day treatment program. Reference should be made to PCT/NZ96/00024 (published as WO 96/29025) of Advanced Animal Technology Limited which relates to the SMARTT1™ product at least in part.

In column 2 lines 52 to 26 WO90/02580 indicates, as an object, the provision of a compact infusion unit which is controlled by electric current supplied by batteries and regulated by means such as an electronic timer, biomedical control means or microprocessor control.

In the SMARTT1™ device each active ingredient is in a liquid form (dissolved in a suitable organic solvent) and is held in a drug reservoir. Each such reservoir is under positive pressure resulting from a spring acting on a plunger or piston. When a solenoid is activated a closure within the solenoid can be opened allowing the liquid to pass from the pressurised reservoir and through a channel running the length of the overall device to be released from its head. By far the bulk of the device (ignoring the variable geometry retention device aspects) are the controller and the pumping mechanisms which occupy greater than 50% of the volume of the device (circuit board, 2AAA batteries, wire, spring, seal, plunger and solid metal components) thus leaving (owing to vaginal tract insertion and retention considerations) the volume of the drug reservoir being limited to about 5 mL.

The present invention in one aspect recognises the desirability, as an alternative to the passive devices, of an active delivery device and in particular although not solely an intra vaginal preferably device useful by way of intra-vaginal insertion of controlling the oestus of animals. Such a device has the prospect of totally delivering its progesterone content.

U.S. Pat. No. 5,318,557 (Elan Medical Technologies Ltd) discloses "smart" pill constructions for insertion into a body cavity and having gas generating means to expand one chamber whilst by contraction of another expressing a substance via an outlet thereof. An electrolytic cell is disclosed as a preferred gas generator.

U.S. Pat. No. 5,354,264 of Insutech, Inc. discloses a drug delivery device which utilises gas pressure from free oxygen and hydrogen derived from the electrolysis of water at the electrodes in negatively charged polymeric hydrogels (E-Gel) in the presence of electro-osmosis. The gas pressure forces the infusion of the drugs through appropriate means into the body with the pressure being dependent on the rate of electrolysis which in turn is controlled by an electric current. This means that the rate of drug delivery can be predetermined and precisely controlled under the action of an electronic timer or a biomedical control system.

U.S. Pat. No. 5,354,264 indicates that the system is made possible through the use of a solid water swollen polymeric hydrogel network having negative charges along the polymer back bone or fixed within the polymer network. The system allows electro-conductivity to occur even when using pure water as the electrolyte. Pure water itself does not have electric conductivity compared to the saline solution taught in Gross et al. European Patent Application 0385915. With the negatively charged polymeric hydrogels of Insutech, Inc. electrical current can be conducted along the negative charges of the polymer backbone. The simple phenomena allows water electrolysis around the electrodes to generate hydrogen and oxygen gas only, free of chlorine or other gases which might be present in the case of saline or other solutions containing electrolyte ions.

Two principals governing the flow of water within the solid hydrogel network and the production of gases at the electrodes are discussed. Example 1 of U.S. Pat. No. 5,354,264 discloses a method of preparation of such a hydrogel.

Reference is also drawn to such transdermal and infusion devices as are disclosed in U.S. Pat. No. 4,969,874 (Disetronic Ag), U.S. Pat. No. 5,090,963 (Product Development (ZGS) Ltd), U.S. Pat. No. 5,527,288 (Elan Medical Technologies, Ltd), U.S. Pat. No. 5,062,834 (Product Development (ZGS) Ltd), and U.S. Pat. No. 5,156,591 (S.I. Scientific Innovations Ltd).

SUMMARY OF THE INVENTION

We have now determined that with a device such as we have hereafter defined, but without the inwardly directed bladder surrounded dip tube modification, that there can be a passive liquid vehicle release such that after (say) a 7 day insertion period in the vagina of (say) a bovine cow approximately 80% of the initial volume is released.

We believe this has implications on the ability to control the release of the liquid vehicle where the control is to be by the generation of a gas to externally pressurise a bladder of the vehicle.

We have also determined that devices of the kind of the present invention not having such a dip tube do not deliver the vehicle in vivo at the same rate observed in vitro.

We have also determined that the provision of a "dip tube" as hereinafter defined is an effective means of providing for a reduction in such passive delivery.

As another example the invention to such devices to dispense liquids into a liquid body such as in reservoirs, fish tank or the like.

Traditionally liquid additions to control the environment of a liquid body (such as that of a fish tank) have been achieved manually by the pouring in of appropriate liquids or by the use of passive release devices such as those including an impregnated matrix from which the desired liquid or liquid bourne active ingredient releases over a period of time.

The present invention is to provide a better control of a release of a desired liquid, (includes emulsions, suspensions, etc.) or to at least provide the public with a useful choice.

In one aspect the present invention consists in a delivery device having a reservoir of variable volume having an outlet through which an included vehicle can be expressed in an liquid form as the volume of the reservoir is actively reduced and wherein there is a tube or equivalent structure ("dip tube") (whether defining said outlet or not) providing a conduit to the outlet from the reservoir of such length and crosssection as to favour active release over passive release.

As used herein the term "outlet" in respect of the reservoir and the term outlet in respect of the dip tube are preferably one and the same. Constructions are envisaged where the tube may be wholly within a structure defining the reservoir, partly within such a structure and partly outside of such structure or even (at least almost) wholly outside of such structure.

The tube in some forms is at least in part within a collapsible bladder (eg; of a latex or other flexible membrane material). In other forms at least part of a cylinder or the equivalent associated with a piston provides the means to reduce the reservoir volume.

Preferably said dip tube is a plastics tube of circular cross-section less than 1 mm in internal diameter.

Preferably the dip tube is such that the passive vehicle release rate of the device is less than 50% (most preferably less than 20%) of the initial volume of vehicle over any insertion period.

Preferably said outlet at least prior to first use is capped.

Preferably said reservoir can be reduced in volume continuously.

Preferably said reservoir can be reduced in volume intermittently.

Preferably the active reduction of the volume is under the action of either.
   i) a gas or gases generated by the application of a controlled or controllable electric current to a water containing matrix contained and/or carried by and/or otherwise associated with the device in such a way as generates free oxygen and free hydrogen (preferably without other gases), or
   ii) a gas or gases generated by the electrolysis of water contained in a hydrogel contained and/or carried by the device (preferably a negatively charged hydrogel which enables hydrolysis of the water which does not otherwise contain free ionic species), Preferably the active reduction is under the action of gas(es) generated by timer and/or microprocessor control of a supply of an electrolysing electric current to a hydrogel.

Preferably the source of electric current is from a battery contained by, carried or otherwise associated with the device.

Preferably said substance is progesterone or a substance having a similar effect.

Preferably said substance is progesterone and the rate of expression enabled, whilst in the vaginal tract of a target mammal, by the content of the bladder, the outlet and the gas generating means is sufficient to first achieve a progesterone plasma level above 2 ng/mL and thereafter maintain a level of at least 2 ng/mL in the mammal for a period of at least 4 days.

Preferably the content of the bladder is from 1 to 60 mL of the delivery liquid.

Preferably said device has a passive delivery rate (over the insertion period) of less than 50% of the initial vehicle volume. Preferably the passive delivery rate is 20% or less.

Preferably, but for the dip tube, the passive delivery rate would be over 20% (and indeed possibly over 50%) of the initial vehicle volume.

Preferably there is sufficient hydrogel to enable an active delivery of greater than 50% (and preferably at least 80%) of the initial vehicle volume of the insertion period.

Preferably the insertion period is at least 4 days.

The device may have a plurality of delivery mechanisms and each or some may be active delivery mechanisms controlled by gas pressure and may include a bladder as opposed to a piston expression.

Preferably said device has a removable seal or cap of said outlet (i) capable of being removed prior to intra vaginal insertion, (ii) which dissolves in the vaginal tract after insertion and/or (iii) which is rupturable under the pressure of the delivery liquid to be released after sufficient gas has been generated by said gas generating means after switch means energising of the circuit.

Preferably said device includes a plurality of such reservoirs of variable geometry each preferably each separately controlled insofar as the expression therefrom of its content is concerned.

Preferably said device is an intra-vaginal device.

Preferably the intra vaginal device is of a variable geometry construction which assists insertion and retention of the device in the vagina of a target species.

Preferably said device includes a plurality of such reservoirs of variable geometry.

Preferably each or several of said reservoirs is separately controlled insofar as the expression therefrom of its content is concerned.

Preferably the expression of progesterone or progesterone containing liquid is substantially continuous and preferably without being pulsile in nature.

Preferably said device includes a number of reservoirs of variable geometry and the substance to the delivered from at least one of the reservoirs of variable geometry is a progesterone.

Preferably the substance to be delivered from at least one other reservoir of variable geometry (whether solid, powder, in a liquid form, or otherwise) are active ingredients such as those hitherto discussed useful in conjunction with progesterone in controlling the synchrony of oestrus in mammals.

Another aspect of the prevent invention consists in a delivery device capable of expressing a liquid vehicle from the outlet of a reservoir, said device having timer and/or microprocessor means, a power source and appropriate circuitry, electrodes and electrolyte matrix to be able to generate a gas from the electrolyte matrix so as to reduce the volume of the reservoir to cause active expression of the vehicle therefrom, there being a tube or equivalent structure ("dip tube") (whether defining said outlet or not) providing a conduit to the outlet from the reservoir of such length and cross section as to favour active release of the vehicle from the reservoir over passive release of the vehicle from the reservoir.

In still a further aspect the present invention consists in a delivery device capable of expressing a liquid vehicle from the outlet of a reservoir, said device having timer and/or microprocessor means, a power source and appropriate circuitry, electrodes and electrolyte matrix to be able to generate a gas from the electrolyte matrix so as to reduce the volume of the reservoir to cause active expression of the vehicle therefrom, there bring a tube or equivalent structure ("dip tube") (whether defining said outlet or not) providing a conduit to the outlet.

Preferably the conduit by capillary or other resistance to passive flow of the vehicle from the reservoir (whether whilst there is any active expression or not) is such as to reduce any such passive egress of the vehicle.

In another aspect the present invention consists in a delivery device, wherein said body has a chamber to an outlet, a bladder within said chamber sealed about said outlet to said body so as to be capable of delivering its contents via said outlet upon the application of gas pressure external of said bladder to the bladder, said bladder containing at least 1 mL (preferably at least 5 mL) of said substance in a liquid delivery form, a tube or equivalent structure ("dip tube") providing a conduit to the outlet from within the bladder (preferably provided to affect the passive leakage rate of the delivery device), and controlled or controllable gas generating means to generate a gas within said body so as to apply gas pressure within said chamber to the exterior of said bladder, and wherein the gas generating means include a hydrogel having electrolysis electrodes, a battery powered circuit capable of applying a controlled or set current to said electrolysis electrodes so as to generate gas from the hydrogel which will have a pressurising effect on the exterior of said bladder, switch means to allow energising of the circuit.

Preferably said "outlet" is as previously defined.

Preferably said device is an intra vaginal device having an elongate body structure coupled to or having resilient means of variable geometry to facilitate in a target mammal vaginal tract insertion, to facilitate vaginal tract retention and to allow vaginal tract withdrawal, when the elongate axis of said body structure is substantially aligned to axis of the vaginal tract.

Preferably said substance is progesterone or a substance having a similar effect.

Preferably said substance is progesterone and the rate of expression enabled, whilst in the vaginal tract of a target mammal, by the content of the bladder, the outlet and the gas generating means is sufficient to first achieve a progesterone plasma level above 2 ng/mL and thereafter maintain a level of at least 2 ng/mL in the mammal for a period of at least 4 days.

Preferably said dip tube is a plastics tube of circular cross-section less than 1 mm in internal diameter.

Preferably said dip tube extends longitudinally of said body structure within said bladder.

Preferably the content of the bladder is from 1 to 60 mL of the delivery liquid.

Preferably said device has a passive delivery rate (over the insertion period) of less than 50% of the initial vehicle volume. Preferably the passive delivery rate is 20% or less.

Preferably, but for the dip tube, the passive delivery rate would be over 20% (and indeed possibly over 50%) of the initial vehicle volume.

Preferably there is sufficient hydrogel to enable an active delivery of greater than 50% (and preferably at least 80%) of the initial vehicle volume of the insertion period.

Preferably the insertion period is at least 4 days.

The device may have a plurality of delivery mechanisms and each or some may be active delivery mechanisms controlled by gas pressure and may include a bladder as opposed to a piston expression.

Preferably said device has a removable seal or cap of said outlet (i) capable of being removed prior to intra vaginal insertion, (ii) which dissolves in the vaginal tract after insertion and/or (iii) which is rupturable under the pressure of the delivery liquid to be released after sufficient gas has been generated by said gas generating means after switch means energising of the circuit.

Preferably said switch means is a manually actuable switch externally accessible prior to the insertion of the device in the vaginal tract of a target mammal.

Preferably said device includes a timer or a logic means which controls the provision of current to the electrolysis electrodes after actuation of said switch means.

Preferably said elongate body structure defines a second chamber in communication with said first chamber and said hydrogel is located in that second chamber.

Preferably said second chamber or an additional chamber locates the battery of said battery powered circuit.

Preferably said elongate body structure includes means remote from the outlet which facilitates the withdrawal of the device from the vaginal tract of a target mammal.

In another aspect the present invention consists in the related methods and use.

In another aspect the present invention consists in a device for releasing a liquid or fluid vehicle [eg; into a liquid body (whether from above or below the surface of the liquid body)], said device comprising a housing defining a cavity, a liquid or fluid (hereafter "liquid") containing bladder located in said housing, said bladder having means providing an outlet capable of discharging its liquid out of said housing, gas generating means disposed within said housing to generate at least partly in said housing gas to impinge upon the exterior of said bladder, and control circuit means to cause a controlled generation of gas from said gas generating means and thus the controlled expression of liquid from said bladder.

Preferably said gas generating means and/or said electrical circuit means comprises a system as disclosed in U.S. Pat. No. 5,354,264 of Insutech Inc and/or U.S. Pat. No. 5,318,557 of Elan Medical Technologies Ltd i.e. an electrolytic cell having electrodes.

Preferably the electrical circuit means to the electrode(s) of said gas generating means, a source of current for said electrical circuit means (e.g. batteries), and means for activating the circuit and thus the energising of said electrode(s).

Preferably said means to control includes a switch and/or programmed logic means.

Preferably said device includes a removable or rupturable seal of said outlet.

Preferably said device is of a kind of sufficient mass so as to be submersible in the liquid into which the liquid of the bladder is to be discharged.

Preferably the liquid of the bladder (whether because of its viscosity, resilience of the outlet or any conduit thereto, size of the outlet or any conduit thereto or otherwise) unless actively expressed by further gas generation leaks (if at all) out of said outlet at a rate below that desired.

In other forms the device is adapted to discharge liquid onto the surface of the liquid.

In some forms of the present invention the device is adapted to discharge liquid from the outlet, the outlet being at an end of a tube, conduit or other passageway leading internally into the bladder.

Preferably said tube is in the form of a dip tube which is adapted to discharge liquid upwardly from within the bladder.

Preferably the device is substantially as hereinafter described with reference to any one or more of the accompanying drawings.

In a further aspect the present invention consists in a method of continuously or incrementally releasing a liquid vehicle, said method involving the use operatively of a device in accordance with the present invention.

Preferably said use involves switching the device on prior to its association operatively with the body of liquid into which or onto which it is to discharge.

Preferably said body of liquid into which or onto which it is to discharge is a fish tank.

BRIEF DESCRIPTION OF THE DRAWINGS

The present invention will now be described with reference to the accompanying drawings in which;

FIG. 4 shows a series of drawings (A) through (E) of a prior art EaziBreed™ CIDR™ product of this company having a progesterone impregnated silicone matrix of an average depth of about 1.5 mm but having the depth thereof varying greatly, FIG. 6 shows a CIDR-B™ form of passive device of this company (NZ Patent Specification No. 286492) having an average progesterone impregnated matrix of about 1 mm thick over a spine of a kind shown in FIG. 2, FIG. 6A shows an elevation of the device of FIG. 3.

FIG. 6B shows the side elevation of the device of FIG. 3A,

FIG. 6C shows a plan view of the top of the device as shown in FIGS. 3A and 6B,

FIG. 6D shows a section at "JJ",

FIG. 6E shows a section at "II",

FIG. 6F shows a section at "KK",

FIG. 6G shows a section at "GG", and

FIG. 6H shows a section at "HH" being the hinging region of the arms from the body, FIG. 6I is the section "LL" of FIG. 6A, FIG. 15 shows the effect of the dip tube arrangement in a device such as in FIG. 12A when there is no gas production and control unit thereby demonstrating vehicle retention/leakage in vivo, FIG. 17 is a plot showing for a hydrogel (E-gel) [upper plot] and aqueous NaCl [lower plot] plots of percent initial current as a function of time.

DETAILED DESCRIPTION OF THE PREFERRED EMBODIMENTS

Figure 1:
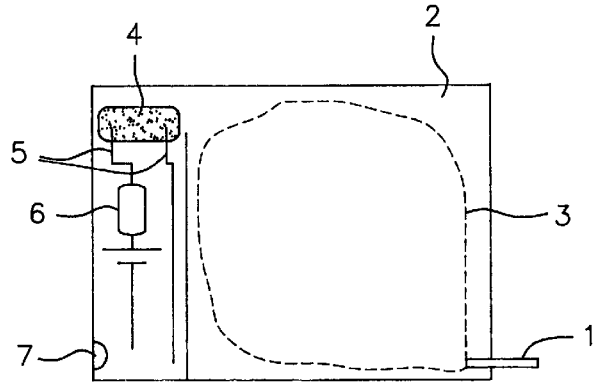
FIG. 1 shows a simple form of the device for dispensing liquids, a bladder within the housing having a direct link by a tube or other means to the exterior of the housing to thus provide the outlet of the bladder.

FIG. 1 shows a device for dispensing of liquids with an outlet orifice 1 exiting from the side of the device. The bladder 3 is disposed in the body cavity 2 of the housing and provides a collapsible reservoir for the agent to be dispensed. An electrolytic cell 4 (e.g. preferably as defined in U.S. Pat. Nos. 5,354,264, 5,318,557, 5,354,264) for the production of gas has electrodes 5. The production of gas is controlled (from preferably the electrolytic hydrogel). The electronic control and power supply unit 6 preferably is activated by a switch 7.

Figure 2:
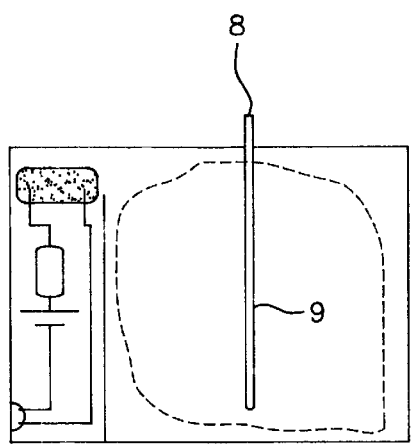
FIG. 2 is a similar arrangement to that of FIG. 1 but showing instead the use of a tube extending internally of the collapsible bladder as the means defining the outlet.

FIG. 2 shows a device for dispensing of liquids with the outlet orifice 8 exiting from the top of the device and extending back into the bladder by a dip tube 9.

Figure 3:
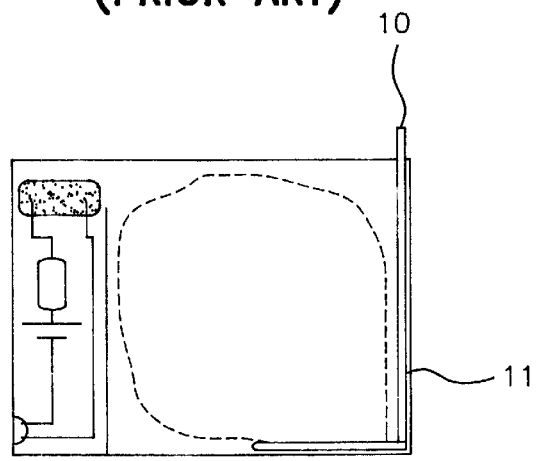
FIG. 3 is still a further embodiment where the outlet is defined by tubes that extend from the bladder out of the housing, the bladder itself thus on its controlled collapse about the liquid it contains discharging the liquid via a significant length of conduiting out of the eventual outlet from the housing.
Figure 4A:
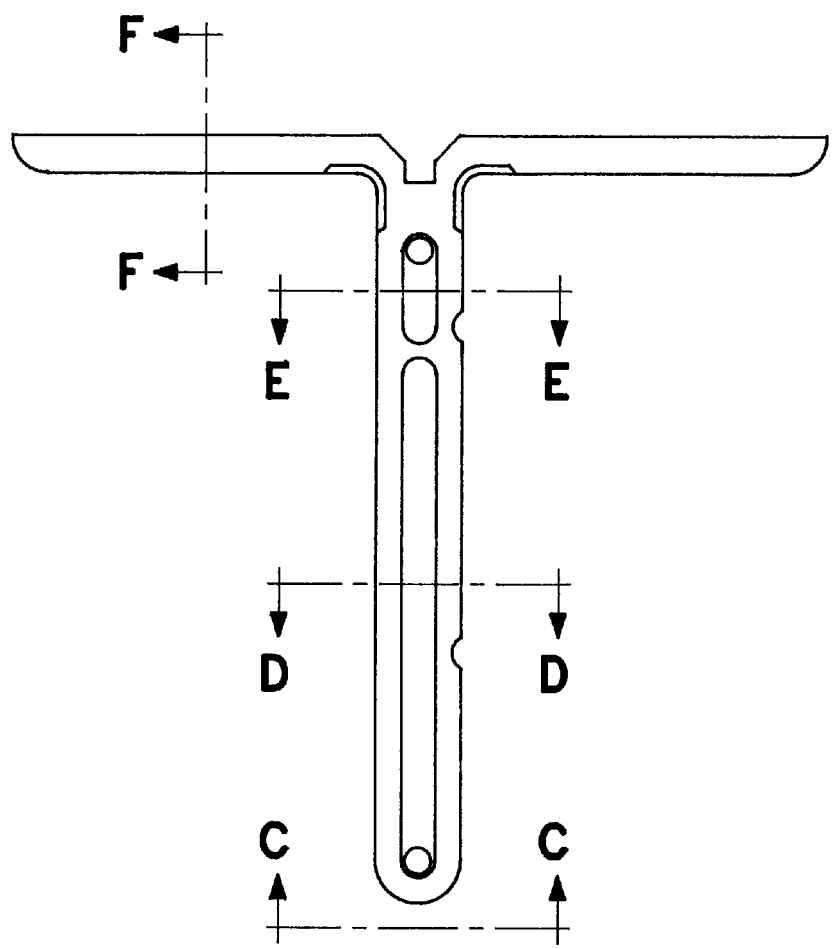
FIG. 4A is an elevation of the "T" shaped device capable of having the top arms thereof resiliently bent to alongside the upstanding body during insertion with an appropriate applicator pull and capable of assuring some return to the "T" form so as to be retained within the vagina of an appropriate animal such as a cattle beast.
Figure 4B:
FIG. 4B is a section at "FF" of the top arms of the "T" form.
Figure 4C:
FIG. 4C is a section at "DD" of the body.
Figure 4D:
FIG. 4D is a view "CC" of the end of the body showing a slot formed therein from a hole through the body so as to allow the lying therein of a retained withdrawal string or other device.
Figure 4E:
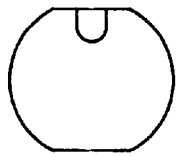
FIG. 4E is a section of the body at "EE"
Figure 5A:
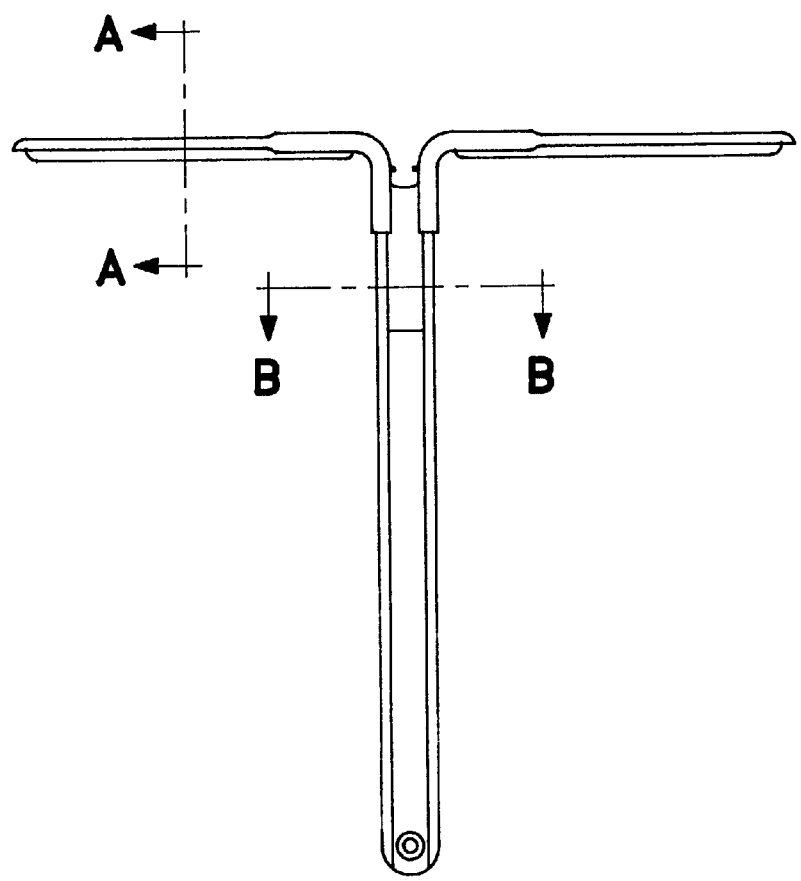
FIG. 5A shows an elevation of the spine, FIG. 5B showing a side elevation of the spine, FIG. 5C showing the plan view of the top arms of the device.
Figure 5B:
FIG. 5 shows the preferred spine of the prior art device, a spine which with no or little modification is useful in a device in accordance with the present invention.
FIG. 5D shows the section at "AA"
FIG. 5E shows the section at "BB"
Figure 5C:
Figure 5D:
Figure 5E:
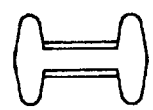
Figure 7A:
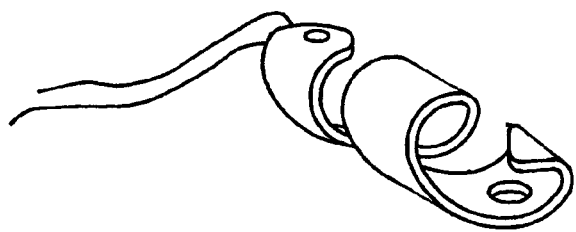
FIG. 7A shows the helical or coil form of the prior art PRID™ device previously referred to, having an optional capsule affixed thereto as previously stated, the device also showing a withdrawal string.
Figure 7B:
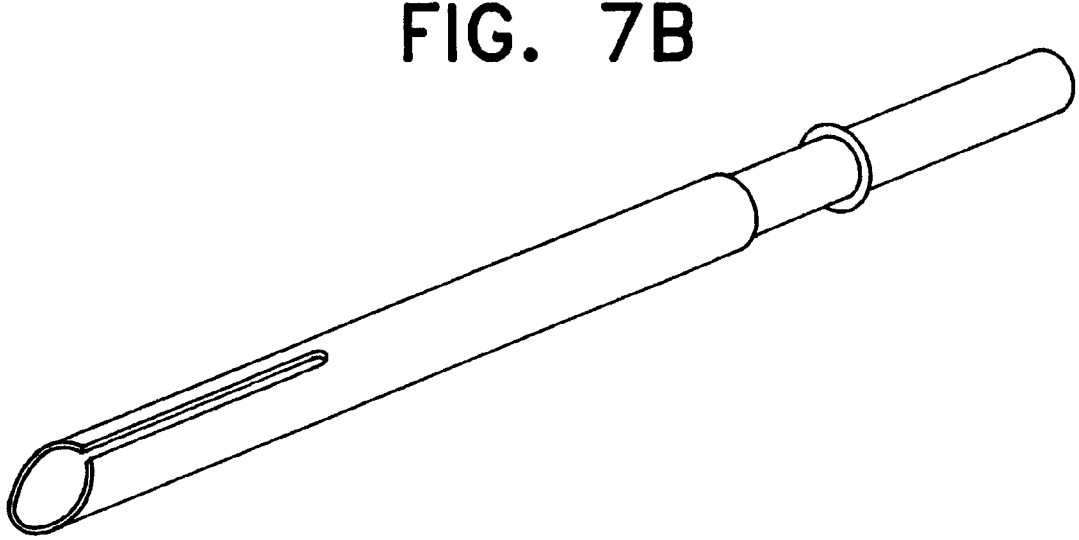
FIG. 7B shows an applicator tool for the device of FIG. 7A.

FIG. 3 shows a device for dispensing of liquids with the outlet orifice 10 exiting from the top of the device and extending back around the bladder and entering the underside of the bladder via a tube 11.

Preferably the housing is formed from a fabricated plastics structure that but for the outlet orifices 1, 8 or 10 of the bladder fully seals the contents, namely the bladder and the gas generating system. The density of the device is such that if desired it can be activated by a switch 7 and thereafter be placed within the body of liquid in which the fish etc. swim to thereafter dispense the liquid from the bladder 3. Appropriate liquids (or fluids) include water or organic solvents containing an active agent, for example an algaecide.

For versions to be immersed or where there is the influence of gravity, a leach out and/or trickle rate (when not being forced by more gas generation) very much less than that required results after the bladder has first responded to some gas generation.

Prior Art Intra Vaginal Devices

The prior art SMART1™ IBD is supplied packaged within a two part application container. Each part is manufactured from polypropylene plastic. The inner part is 89 mm in length, 39 mm (o.d.), 37 mm (i.d.) in diameter, and 1 mm in thickness. It has a hole in its base 26 mm in diameter through which the device and tail can protrude. The outer part is 120 mm in length, 1 mm in thickness and 41 mm (o.d.), 39 mm (i.d.) In diameter. It tapers to a rounded shape at its top end. Groves are cut into the tapered round end allowing this part to flex open allowing the device to pass through it upon administration. Also attached to the outer part of the applicator container are hinged wings which rest against the device in the folded position. These wings are each 30 mm in length and designed to be opened, and rest upon the lips of the vulva, upon administration of the device. The SMARTT1™ IBD device fits snugly into the inner part of the application container which in turn fits snugly into the outer sheath of the device. Thus the application container affords protection of the SMARTT1™ IBD device on storage and handling and also holds the retention wings in a folded position during storage.

The SMARTT1™ IBD device itself comprises (i) an outer plastic sheath designed to protect the inner compartment and delicate electronics and (ii) the inner compartment which contains an electronic chip and board, has four drug reservoirs (one at the base of the device and three sited at the head of the device), engages a retention mechanism and has a tail.

The outer sheath is made of plastic (high density polyethylene) and is 131 mm in length and has a diameter of 25 mm at its upper opening. The outer sheath tapers about midway along its longitudinal length to a diameter of 20 mm. The bottom of the sheath has 5 mm diameter hole to allow the tail to pass through. The tail of plastic (high density polyethylene) extends 226 mm behind the device and is 2 mm in diameter and appears relatively inflexible. At the terminal end of the tail is a flattened portion 22 mm in length, 5 mm wide and 2 mm deep. Integrated into the moulding of the tail at its top end is a round plug containing grips. This plug is designed to fit tightly into the base of the device and the grips are designed to prevent it from falling out. This mechanism fixes the tail to the device and prevents it from loss during storage, when activated and during removal from the animal.

The retention mechanism comprises eight fixed prongs made from Hytrel evolving from a central circle each at an angle of 40°. Each prong is 51 mm in length and 2 mm deep by 3.5 mm wide. At the terminal end of each prong is a circular protective ball 6 mm in diameter. This ball affords protection to the delicate vaginal mucosa during the insertion and retention of the device during the treatment period. The retention mechanism is located at the head of the device.

The inner compartment contains a "large" drug reservoir that runs approximately half the length of the device. At the top end of the reservoir is a small orifice which is opened and closed by a switch mechanism which is operated by a solenoid. In the closed position the switch is designed to prevent drug solution from leaving the drug reservoir. In the open position drug solution is allowed to freely flow through a small orifice which leads to a small bore stainless steel opening (absolute diameter unknown but <0.45 mm i.d.). To the exterior at the flat face of the head of the device. This large drug reservoir is circular in shape, 18 mm in diameter and 22 mm in length. It has a capacity to hold a total volume of 5 mL of distilled water, The solution is prevented from escaping from the bottom of the device by a tight fitting SANTOPRENE rubber seal. Between the rubber seal and the bottom of the device is a movable plunger and spring which is 80 mm in length when uncoiled and of unknown tension. The device has been designed to allow the organic solution to be released from this large drug reservoir over a 10 day period.

Three other drug reservoirs are in the device (the "small reservoirs"). The reservoirs are located at the head of the device. They are sited equidistant around the flat face of the head of the device and are each of equivalent shape and size being ovoid in shape, 7.5 mm wide and 5 mm across and 16 mm in depth (with the rubber seal in place; 19 mm with the seal removed). Each of these drug reservoirs has the capacity to hold a total volume of 0.45 mL of distilled water (with the rubber seal in place). Drug solutions are prevented from leaking from the small reservoirs during storage and while in the animal by tight fitting rubber SANTOPRENE rubber) seals located at the head of the device. Only two of the small drug reservoirs are utilised and contain drug solutions in the SMARTT1™ IBD device.

The remainder of the device comprises a circuit board and 2 batteries (Type AAA) lying parallel with and under to the left and right of the circuit board. The circuit board contains components primarily consisting of a controlling chip, a power-on indicating LED and a quartz timer.

A plastic tag of variable length and 8 mm width is inserted between the positive end of the left AAA battery and the battery terminal of the device. It is of sufficient length to protrude beyond the head of the device. Removal of this tag activates the device. The circuit board and the battery terminals are coated in a generous layer of silicone grease to prevent moisture coming into contact with the electronic componentry of the device.

To operate the device in the field the device must first be removed from the applicator container in order to turn it on. In addition, to achieve activation of the device, the device itself must be dismantled. This entails partial removal of the outer sheath to enable removal of the plastic strip. After re-assembly of the outer plastic sheath onto the inner compartment and locking it over the retaining clamps, the device is then re-inserted into the applicator container and loaded onto the applicator gun. The rounded end of the applicator container is then lightly lubricated and pushed approximately 30 mm inside the vagina until the wings of the application container lie flush with the lips of the vulva. Pressure is then applied to the device by pushing the applicator gun. This results in the device being inserted into the anterior vaginal close to the cervix. To remove the device at the end of the treatment period the protruding tail is pulled gently but firmly until the device is removed.

TABLE 3

Summary of the three drug reservoir vehicles

| Reservoir | Vehicle odour | Vehicle colour | Active agent stated by Plade Holdings |
|---|---|---|---|
| Large | Benzaldehyde | Straw | Progesterone |
| Small reservoir 1 | Alcoholic | Clear | Oestradiol benzoate |
| Small reservoir 2 | Aniseed | Clear | Cloprostenol sodium |
| Small reservoir 3 | Empty | Empty | Empty |

Mechanism of Oestradiol Benzoate and Cloprostenol Sodium Release from the SMARTT1™ IBD The contents of the small reservoirs are found to be released by the following mechanism. The reservoirs contain a spring loaded plunger which is pulled back and held in the loaded position. This is achieved by locking it in place by a retaining cord which rests over a resistor located on the electronic board. The resistor located under the cord retaining the plunger is activated at a pre-programmed time under the control of the circuit board chip. Upon activation the resistor heats up and the cord burns through and severs. The plunger is therefore no longer under tension and the contents of the reservoir are violently expelled by the sudden relaxing of the spring pushing against the plunger.

Mechanism of Progesterone Release from the SMARTT1™ IBD

The mechanism of release of the progesterone containing vehicle relies upon (i) a large spring located at the base of the device which forces a moveable plunger through the reservoir, (ii) a small orifice and (iii) a solenoid. Progesterone containing vehicle is released through a small orifice which leads to a length of small bore tubing which opens at the head of the device. The opening and closing of the orifice controls how much vehicle is released and this in turn is controlled by a solenoid which opens and closes the small orifice. When the solenoid is activated the closure pulls back against the force of a small spring and opens the orifice that leads to the small bore tubing. The frequency of opening and closing of the orifice follows a pre-defined program which is controlled by the micro chip. When the solenoid is activated the orifice opens during which time the progesterone containing vehicle is allowed to travel through the orifice, up the small bore tubing and out of the opening at the head of the device. When the solenoid is turned off a small spring pushes forward and seals the opening and no progesterone release occurs.

Figure 9:
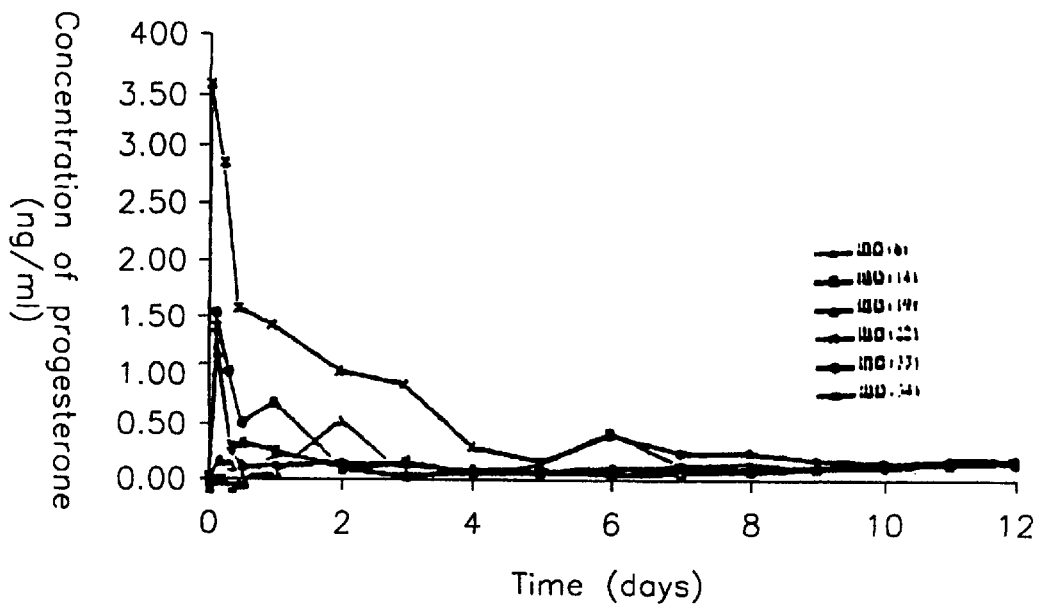
FIG. 9 is the plot for the plasma levels for the SMARTT1™ IBD.

Plasma Levels of Progesterone Following 12 Day Insertion of the SMARTT1™ IBD Device The plasma progesterone levels for six ovariectomised cows with SMARTT1™ IBD inserted for 12 days are shown in FIG. 9. The profiles for each device typically show an initial rise in plasma progesterone levels immediately following insertion (the magnitude of which shows considerable variation between animals), decreasing to concentrations close to basal levels on about day 4. Plasma levels then remain at this low level until device removal.

Deliveries from Small Reservoirs of the SMARTT1™ IBD Device

In vitro trialing showed reliable release at preprogrammed times. Reliability in vivo inconclusive owing to unreliability of the progesterone deliveries and their effects on the recipient animals.

The Present Invention

The pump system of the present invention occupying less space could replace much of the pumping mechanism of the SMARTT1™ eg. plunger, spring and solenoid, and thereby can increase the drug reservoir to 60 mL or more.

The following table (Table 4) outlines parameters in respect of the progesterone delivery aspects, a preferred device of the present invention preferably operates at:

TABLE 4

| Parameter | Value |
| --- | --- |
| dose rate (mg/day) | 70 |
| period (days) | 5 |

TABLE 4-continued

| Parameter | Value |
| --- | --- |
| total volume (mL) | 8 |
| delivery rate (mL/day) | 1.6 |
| pump rate (mL/hr) | 0.07 |

The CIDR-B™ delivers progesterone at a rate of approximately 70 mg/day.

A device of the present invention is believed to achieve the following delivery rates (Table 5).

TABLE 5

| Infusion (70 mg/day) | Delivery rate (mL/hr) |
| --- | --- |
| i.v. emulsion (0.81 mg/mL) | ~5 |
| i.vag. Emulsion (0.67 mg/mL) | ~5 |
| i.vag. alcoholic solution (0.1 mg/mL) | ~30 |
| i.vag. aqueous solution (0.01 mg/mL) | ~300 |

It has been suggested that the device could be provided with reservoirs used for the pulsile delivery of drugs, immediately on and/or a number of days after administration.

The present invention is depicted in a number of different embodiments in

FIGS. 10 through 12, 18A and 18B.

In these drawings the reference numerals denote the following;

(12) drug reservoir chamber,

(13) outlet (preferably simply a small opening) (preferably an opening from which a cover has been removed prior to initiation),

(14) a bladder (e.g. of latex),

(15) or (H) a gel of the kind previously described,

(16) a controller device embodying, if any, the appropriate logic circuit (analogue or microprocessor) preferably having source of power, (eg; one or more batteries) and providing appropriate energisation as required to the electrodes,

(17) the electrodes,

(18) a switch preferably capable of being activated simply to initiate the device prior to insertion,

(19) the dip tube

(20) variable geometry retention members or wings (B) a battery (R) or (VR) a resistor or variable resistor respectively (P) a plug for the outlet (T) a removable seal for the outlet.

Figure 10:
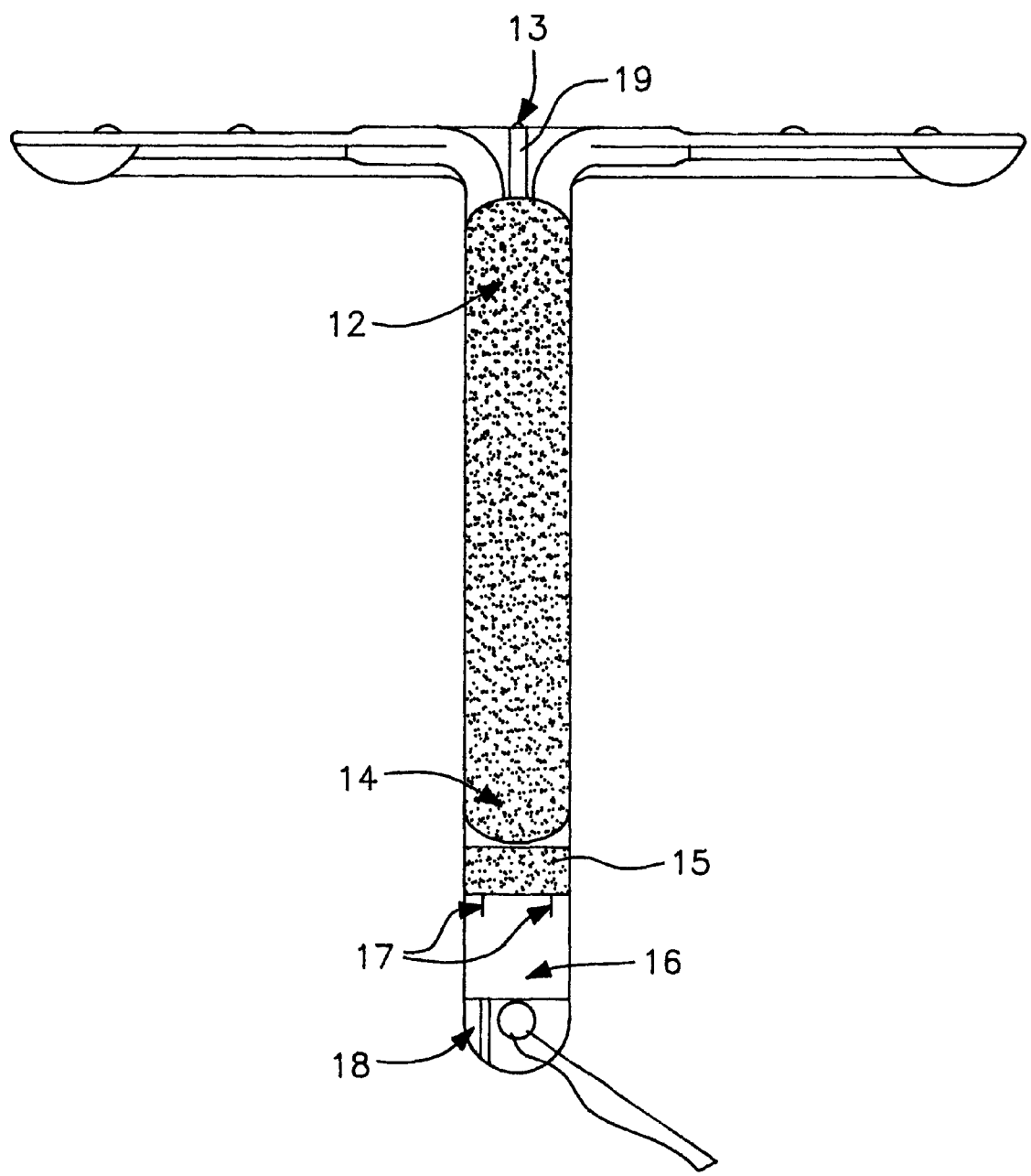
FIG. 10 is an intra vaginal active release device having a bladder as the means by which the drug reservoir is to be reduced in volume under the action of the generated gas.

FIG. 10 shows a device for insertion into the vagina with an outlet orifice 13 for the expulsion of vehicle from a reservoir 12 formed by an internal cavity in the body of the device, with a bladder 14 defining the liquid vehicle filled reservoir, behind which is an electrolytic cell for the production of gas with electrodes 17 inserted into the electrolytic cell, the production of gas being controlled and powered by the electronic control and controller device 16 which is activated by a switch 18.

Figure 11:
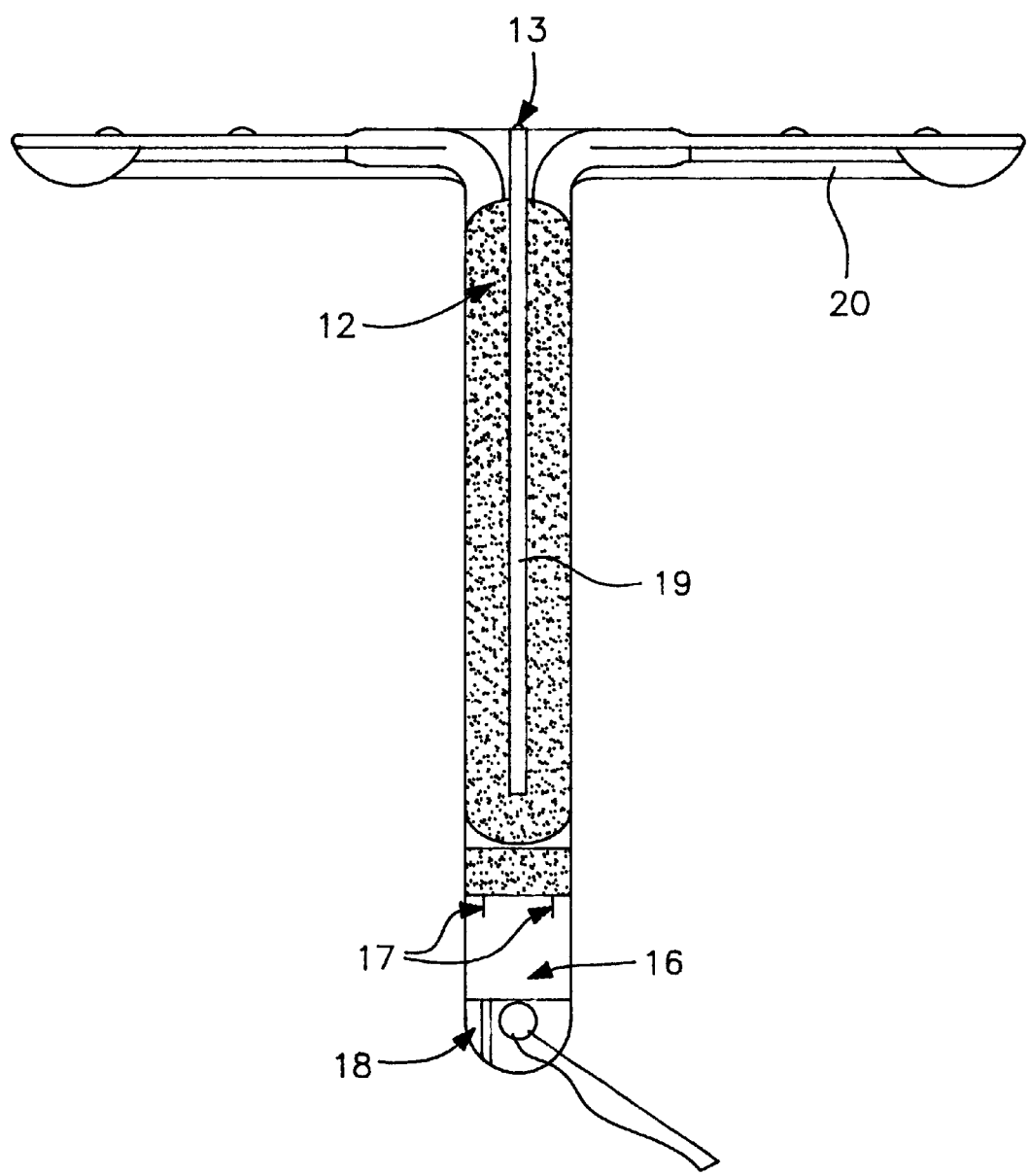
FIG. 11 shows a dip tube (or extended dip tube) arrangement for a device of FIG. 6.

FIG. 11 is the preferred dip tube (19) variant of the device of FIG. 10.

FIG. 12 shows a preferred form of the device where a single vehicle is to be released via a dip tube 19 whilst being retained in the vagina by variable geometry wing or the equivalent 20, the device being of a kind having a collapsible latex bladder 14.

Figure 8:
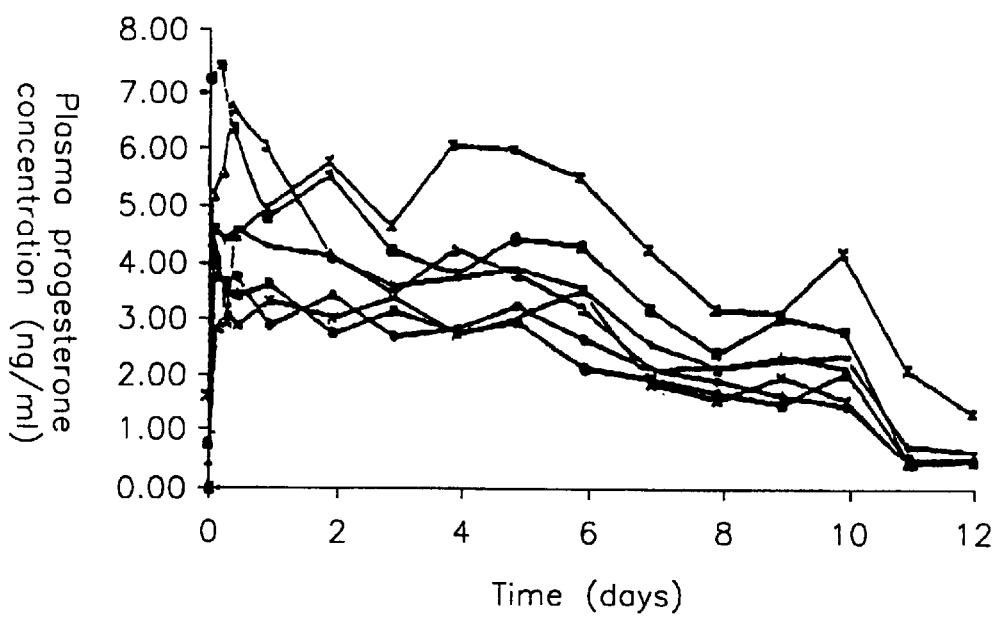
FIG. 8 is the plot for the plasma levels for the CIDR-B™ device.

| Preferred dimensions of the FIG. 12 device are: | |
| --- | --- |
| length of body | from 50 to 250 mm, preferably 150 mm. |
| length of wings | from 40 to 250 mm, preferably 150 mm. |
| diameter of body | from 5 to 60 mm, preferably 25 mm. |
| material of body | a rigid material such as rigid PVC tubing. |
| materials of wings | a rigid material such as PVC, or a material with a degree of softness such as silicone rubber. |
| Preferred hydrogel material and volume for a device of FIG. 8 are: | |
| volume | from 0.1 to 50 mL, preferably 1 mL. |
| material | a polymer or combination of polymers possessing gelling abilities and negatively charged groups, preferably agarose (obtainable from Sigma Chemical Co, USA - Product code A-6013) and dextran sulfate (obtainable from Sigma Chemical Co. USA - Product code D-4911). |

FIGS. 12A through 12D shows the collapse sequence customarily expected from a device of this kind.

Figure 12A:
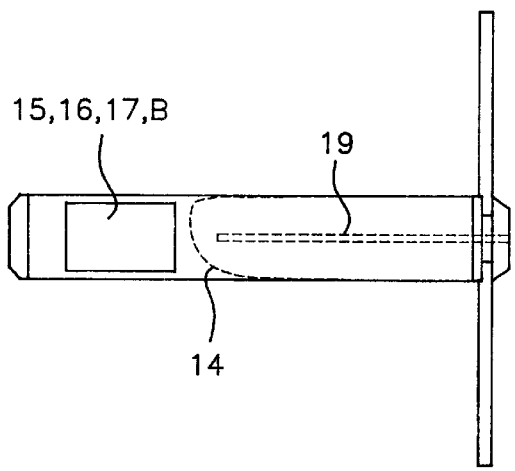
FIG. 12 is a preferred form of a device for single drug delivery with deployable wings also having a dip tube arrangement, the sequence of FIGS. 12A to 12D (not showing the mechanism of retention) showing the mode of dispensing via the dip tube under the gas induced collapse of a latex bladder.
Figure 12B:
Figure 12C:
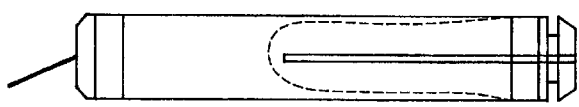
Figure 12D:
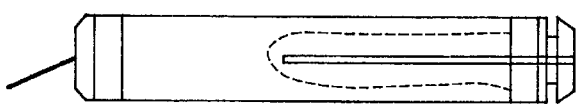
Figure 12E:
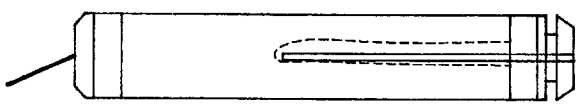
Figure 13:
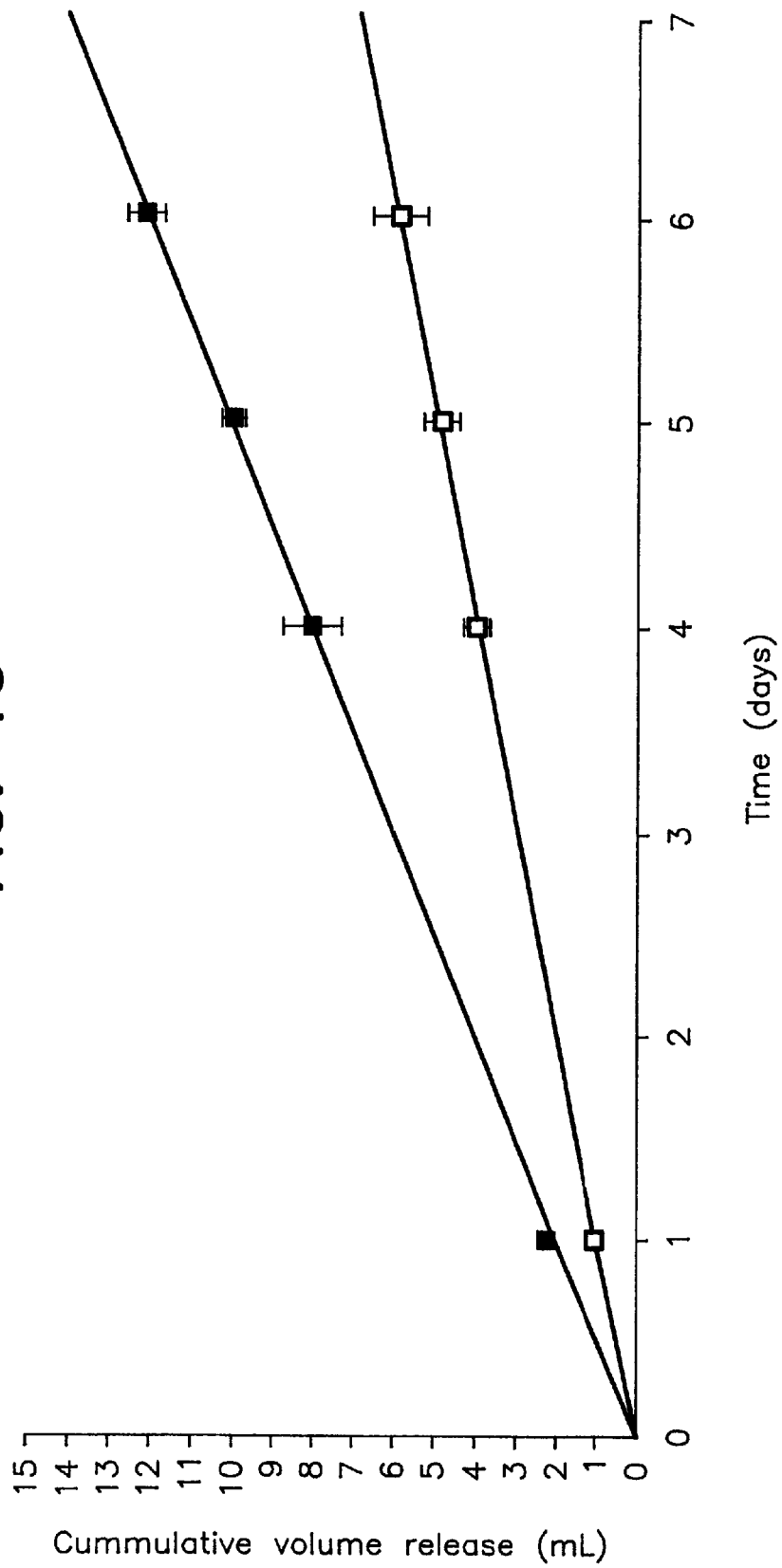
FIG. 13 is a plot for the device of FIG. 12A showing in vitro release rate of the device for two different currents to the gas generating hydrogel.

FIG. 13 shows the in vitro release rate of a liquid vehicle from a device as shown in FIG. 12 using two different currents and thus rates of gas production. In the plot of cumulative volume released (milliliters) against time (days) a lower current of 250 mA is shown below an upper line for a current of 500 mA.

The rate of gas produced during electrolysis in an electrolytic cell is proportional to the applied current. Therefore a constant current is required to achieve a constant and controlled rate of gas production. FIG. 17 displays the current observed through two types of electrolytic cell (using a circuit as per FIG. 16A) over a period of 7 days. The current through an electrolytic cell containing the hydrogel was observed to be constant, varying by less than 6% of the initial (t=0) current, suggesting a controlled rate of gas production. However current through an electrolytic cell containing saline (NaCl) was observed to steadily decline over the observation period by 14% of the initial (t=0) current suggesting a decreasing and thus uncontrolled rate of gas production.

Figure 14:
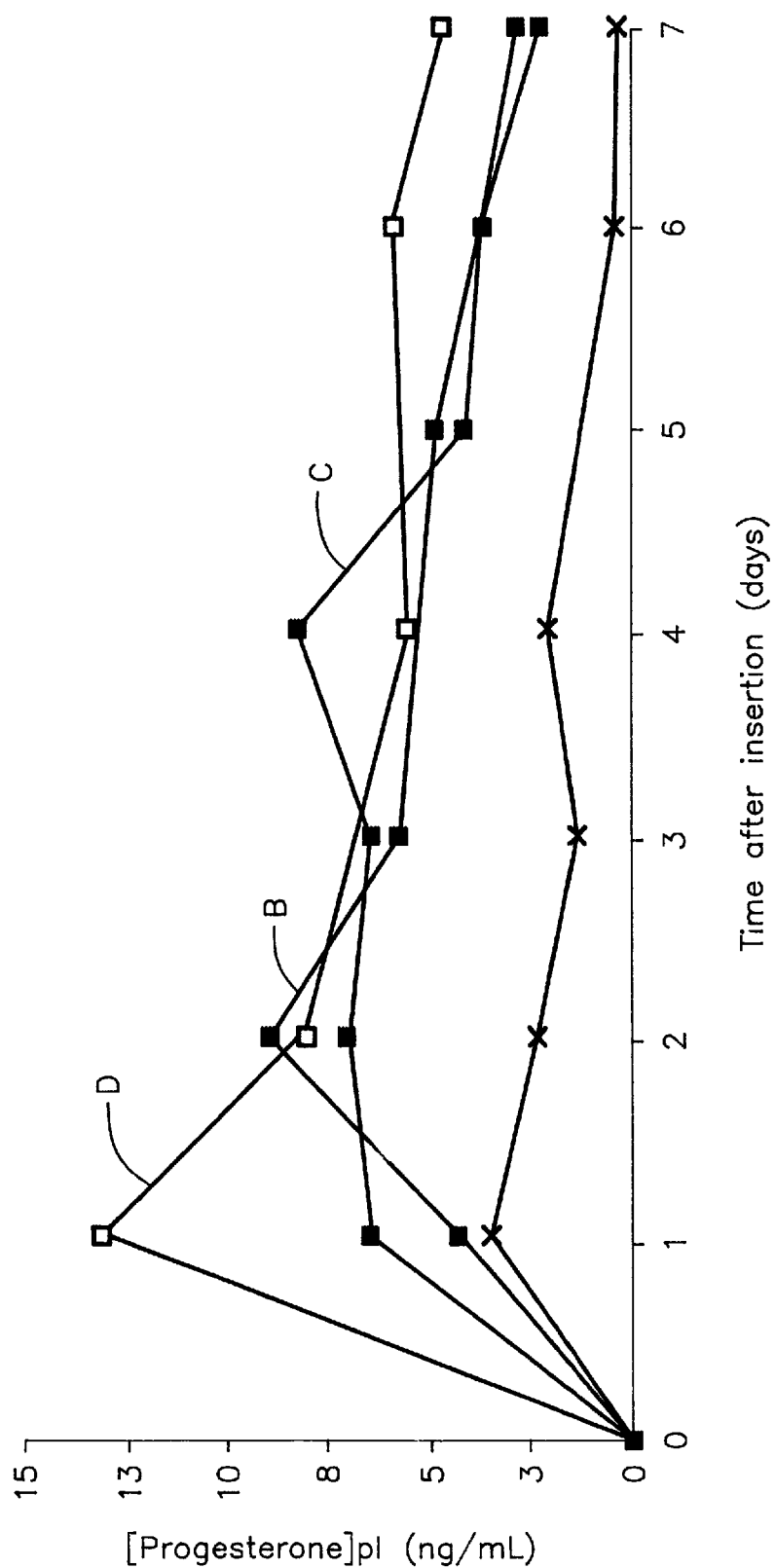
FIG. 14 shows for a device of FIG. 12A plasma progesterone levels (two with and one without a gas and control production unit) against the performance of a CIDR-B™ device of applicant.

FIG. 14 shows on a plot of progesterone plasma levels (mg/mL) against time after insertion of the device in days. The line "A" is of a device as shown in FIG. 12 without a gas production and control unit The lines "B" and "C" are two plots of the performance of a device as shown in FIG. 12 each with a gas production and control unit. By way of comparison the line "D" shows the performance of a conventional CIDR-B™ device of this company.

Intra vaginal delivery devices of the type shown in FIG. 12 that do not possess a dip tube passively release vehicle contained in the bladder at such a rate that after a 7 day insertion period in the vagina of cattle approximately 80% of the initial volume of vehicle is released. This has implications on the ability to control the release of vehicle by controlling the rate of gas production (ie; current) and therefore the flow rate of vehicle. Devices that do not possess a dip tube do not deliver vehicle in vivo at the same rate observed in vitro (see Table 6), Passive leakage should be kept to a minimum in order to differentiate between selected currents and therefore flow rate of vehicle. An acceptable minimum passive release is less than 20% of the initial volume of vehicle over any insertion period.

TABLE 6

| In vitro release rate | Current (mA) | | In vivo release of vehicle after a 7 day insertion period (mL) | | |
| --- | --- | --- | --- | --- | --- |
| (mL) | Initial | Final | Initial | Final | Release |
| 1 | 0.25 | 0.24 ± 0.01 | 13.5 ± 0.7 | 1.8 ± 2.1 | 11.7 ± 1.6 |
| 2 | 0.50 | 0.53 ± 0.02 | 14.8 ± 0.8 | 0.1 ± 0.0 | 14.7 ± 0.7 |

FIG. 15 shows the effect of a dip tube arrangment upon the in vivo retention of vehicle when there is no gas production and control unit. If no dip tube arrangement is present as depicted by the lower end approximately 80% of the vehicle is lost in vivo due to passive leaking from the delivery orifice. This is to be compared with the upper line which shows the same apparatus but with a dip tube arrangement as shown in FIG. 8A present. In this instance only about 30–40% of the vehicle is lost owing to passive leaking.

Figure 16A:
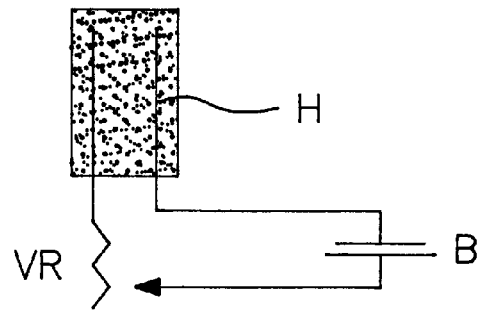
FIGS. 16A and 16B show a resistor controlled circuits for providing current to the hydrogel electrodes.
Figure 16B:
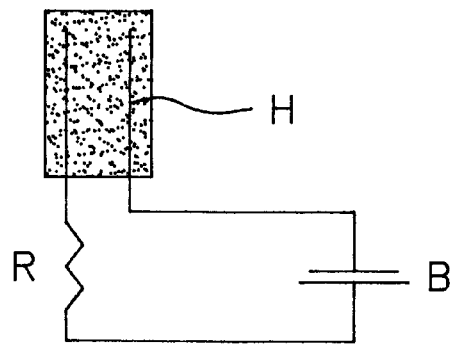

FIGS. 16A and 16B show a simple circuit to the electrodes of the hydrogel H, the circuits have in each instance a battery B (of any suitable kind) and a fixed resistor R or a variable resistor VR.

Figure 18A:
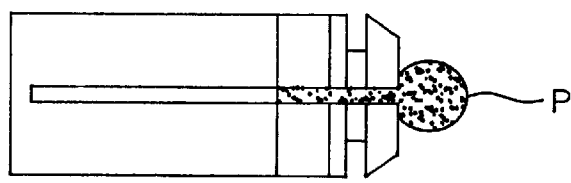
FIGS. 18A and 18B show two forms of sealing arrangement for the outlet of a device.
Figure 18B:
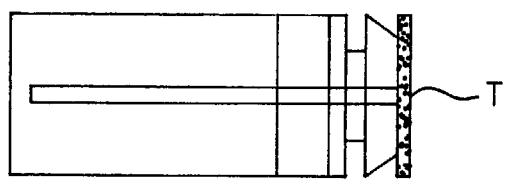

FIGS. 18A and 18B show preferred methods of sealing the delivery outlet of devices of the type shown in FIG. 12. FIG. 18A shows a plug "P" that is inserted into the delivery outlet and is designed such that a closed fitting seal is created. A tag or suitable means can also be incorporated for removal of the plug. FIG. 18B shows a removable seal T that is placed over the delivery outlet, the film may be retained by means of a suitable adhesive. Removal of the seal is achieved when the overlapping edges of the seal are pulled away from the delivery outlet immediately prior to intra vaginal insertion.

When devices of the type depicted in FIG. 12A containing an aqueous or alcoholic vehicle with or without a dip tube connected to the delivery orifice are inserted into the vagina of cattle for 7 days the following volume losses are recorded. The dip tube is found to reduce the amount of vehicle lost, FIG. 19.

Figure 19:
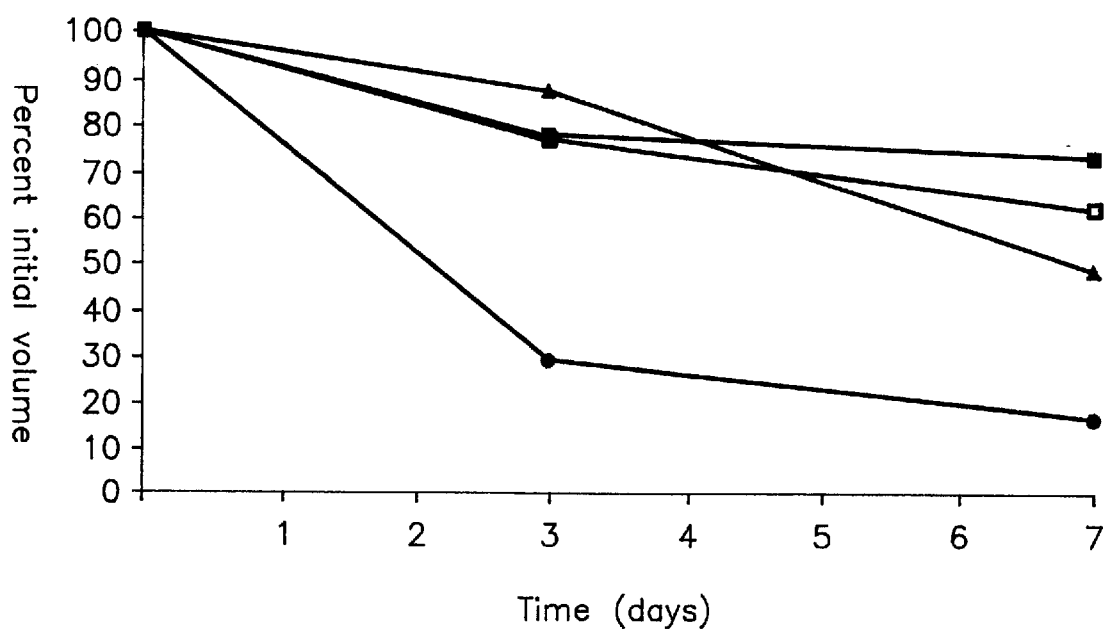
FIG. 19 shows a passive release of aqueous (square symbols) or alcoholic (diamond symbols) vehicle following insertion into the vagina of cattle for 7 days from such a device as depicted in FIG. 12A with (closed symbols) a 7 cm long dip tube or without (open symbols) a dip tube.

FIG. 19 shows a passive release of aqueous (square symbols) or alcoholic (diamond symbols) vehicle following insertion into the vagina of cattle for 7 days from such a device as depicted in FIG. 12A with (closed symbols) a 7 cm long dip tube or without (open symbols) a dip tube.

Figure 20:
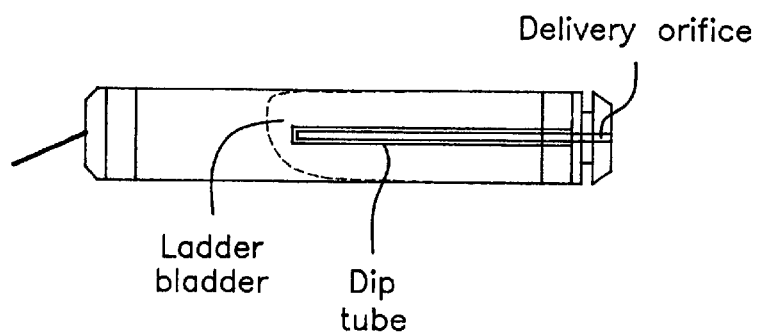
FIG. 20 shows a device for release of liquid vehicle from a collapsible reservoir for which the passage of vehicle is along a dip tube from the interior of the device to the external environment, the dip tube being of length greater than the length of the bladder and therefore is positioned such that portions of the dip tube may lay adjacent to itself.

FIG. 20 shows a device for release of liquid vehicle from a collapsible reservoir for which the passage of vehicle is along a dip tube from the interior of the device to the external environment. The dip tube in such a device as this is of length greater than the length of the bladder and therefore is positioned such that portions of the dip tube may lay adjacent to itself.

Figure 21:
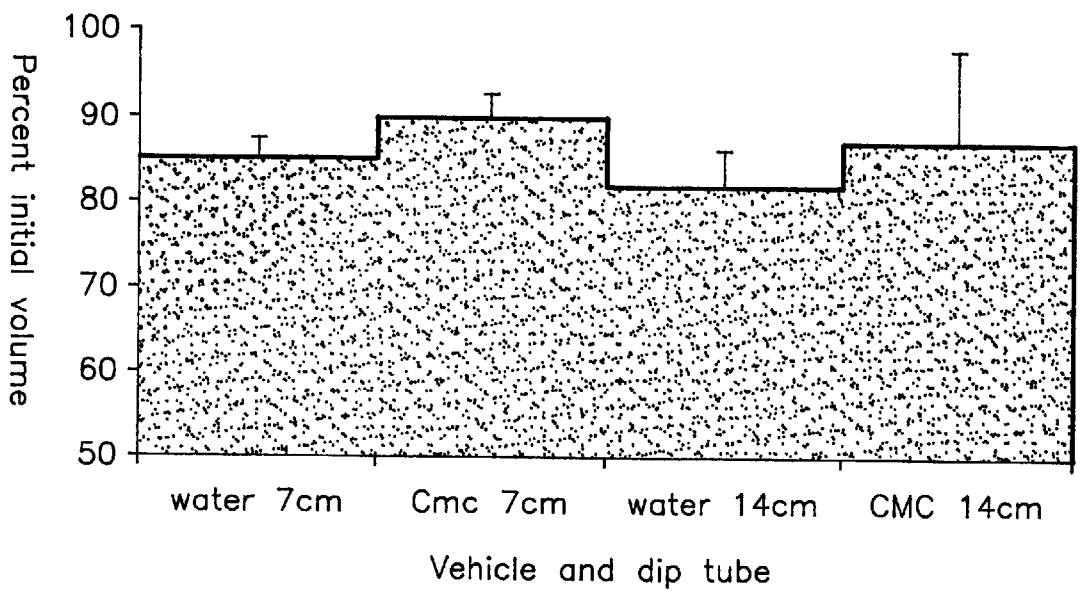
FIG. 21 is a dependence of passive release as a function of dip tube length, water and carbovy methyl cellusose (cmc)

When devices of the type depicted in FIG. 12A and FIG. 20 containing an aqueous vehicle with or without carboxymethylcellulose and a dip tube of 7 or 14 cm connected to the delivery orifice are inserted into the vagina of cattle for 7 days the volume losses shown in FIG. 21 are recorded.

Figure 22:
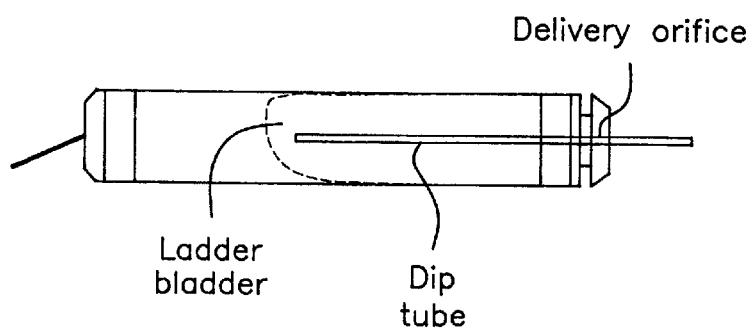
FIG. 22 shows a device for release of liquid vehicle from a collapsible reservoir for which the passage of vehicle is along a dip tube from the interior of the device to the external environment, the dip tube being of length greater than the length of the bladder and is positioned such that a portion of the dip tube extends beyond the bladder.

FIG. 21 is a dependence of passive release as a function of dip tube length, water and carbovy methyl cellusose (cmc), FIG. 22 shows a device for release of liquid vehicle from a collapsible reservoir for which the passage of vehicle is along a dip tube from the interior of the device to the external environment. The dip tube in such a device as this is of length greater than the length of the bladder and is positioned such that a portion of the dip tube extends beyond the bladder.

Figure 23:
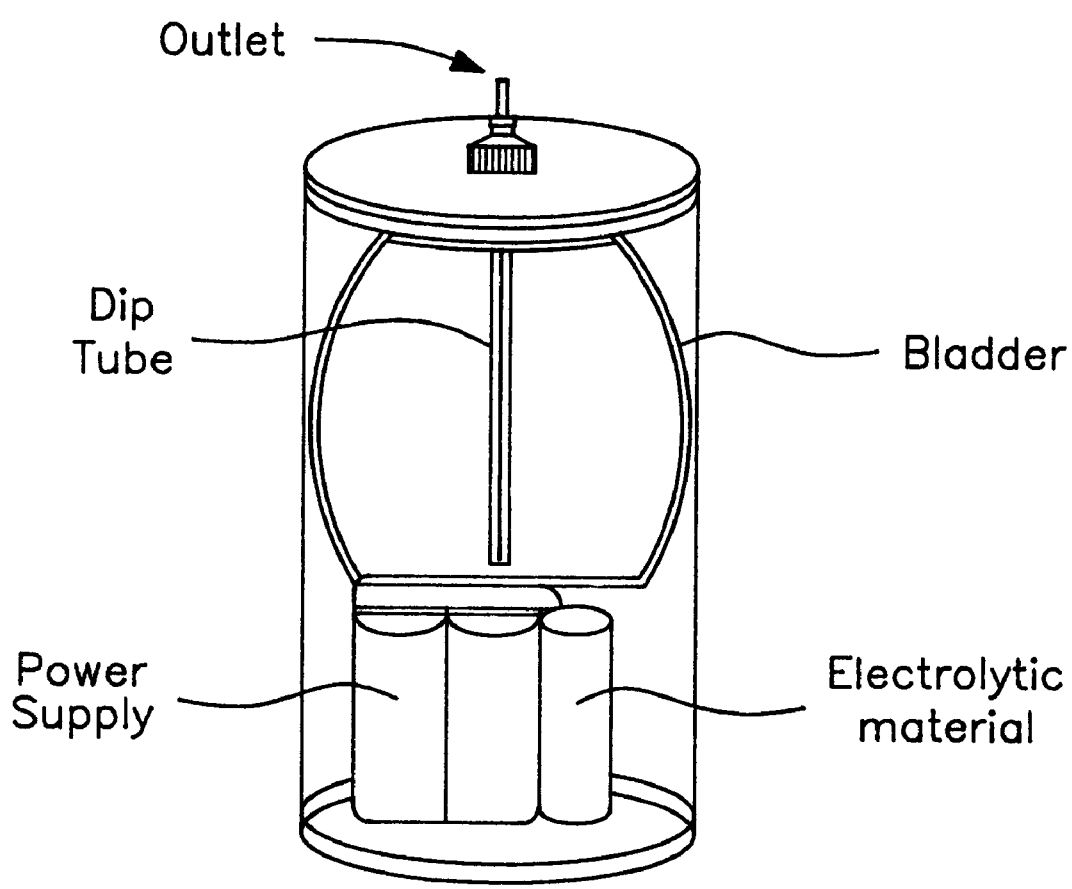
FIG. 23 is a device for release of liquid vehicle from a collapsible reservoir for which the passage of vehicle is along a dip tube from the interior of the device to the external environment.

FIG. 23 is a device for release of liquid vehicle from a collapsible reservoir for which the passage of vehicle is along a dip tube from the interior of the device to the external environment.

Figure 24:
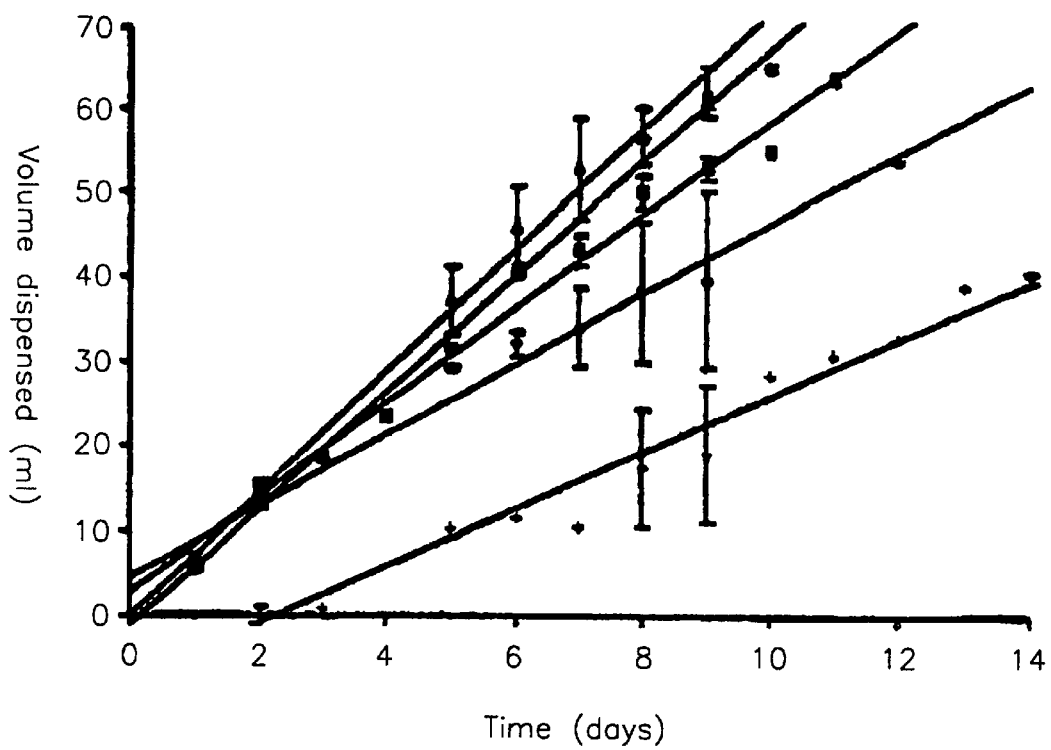
FIG. 24 shows an average volume of water dispensed from such a device as depicted in FIG. 23 against time for devices with different outlet orifices 0.10 (+), 0.18 (♦), 0.25 (■), 0.51 (●) and 1.02 (▲) mm. Error bars are standard error means (n=3)

FIG. 24 shows an average volume of water dispensed from such a device as depicted in FIG. 23 against time for devices with different outlet orifices 0.10 (+), 0.18 (♦), 0.25 (■), 0.51 (●) and 1.02 (▲) mm. Error bars are standard error means (n=3).

Figure 25:
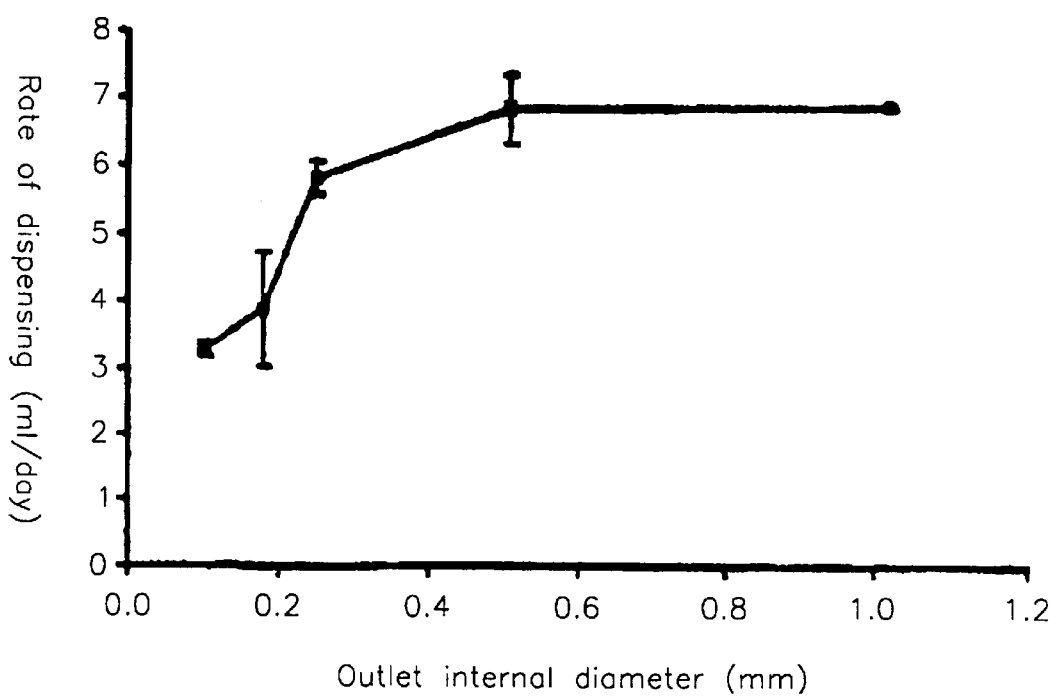
FIG. 25 shows an average rate of water dispensed from such a device as depicted in FIG. 23 against outlet internal diameter. Error bars are standard error means (n=3)

FIG. 25 shows an average rate of water dispensed from such a device as depicted in FIG. 23 against outlet internal diameter. Error bars are standard error means (n=3).

Figure 26:
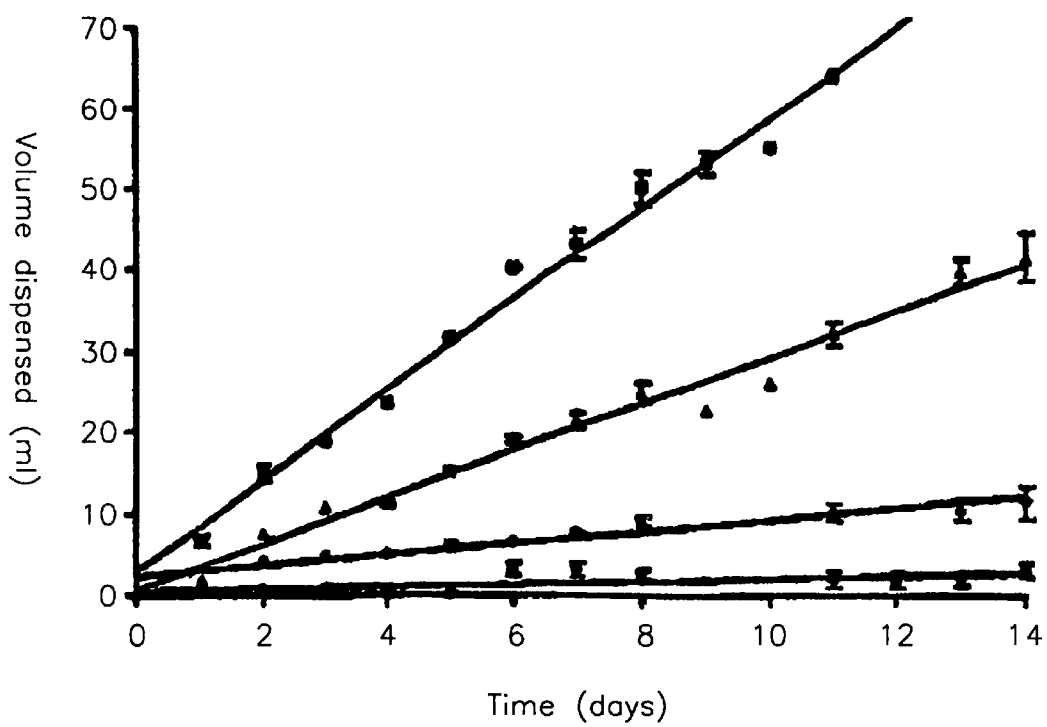
FIG. 26 shows an average volume of water dispensed from such a device as depicted in FIG. 23 against time for devices with different currents of electrolysis 0 (●), 0.1 (♦), 0.3 (▲) and 0.5 (■) mA. Error bars are standard error means (n=3)

FIG. 26 shows an average volume of water dispensed from such a device as depicted in FIG. 23 against time for devices with different currents of electrolysis 0 (●), 0.1 (♦), 0.3 (▲) and 0.5 (■) mA. Error bars are standard error means (n=3).

Figure 27:
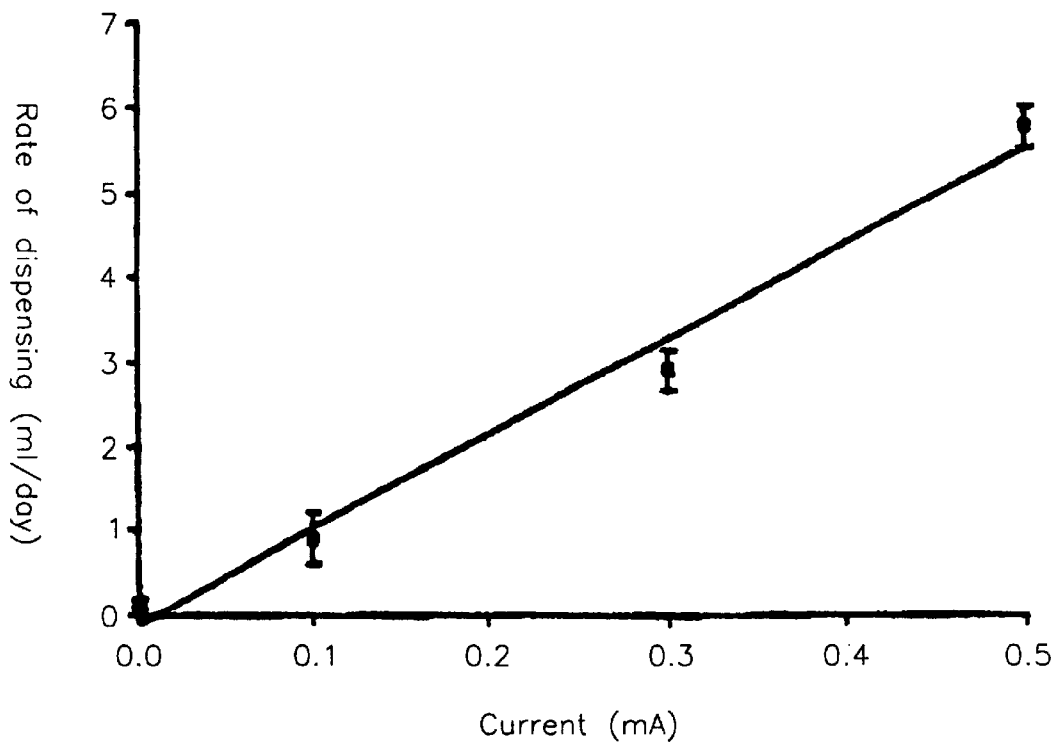
FIG. 27 shows an average rate of water dispensed from such a device as depicted in FIG. 23 against current of electrolysis. Error bars are standard error means (n=3)

FIG. 27 shows an average rate of water dispensed from such a device as depicted in FIG. 23 against current of electrolysis. Error bars are standard error means (n=3).

Figure 28:
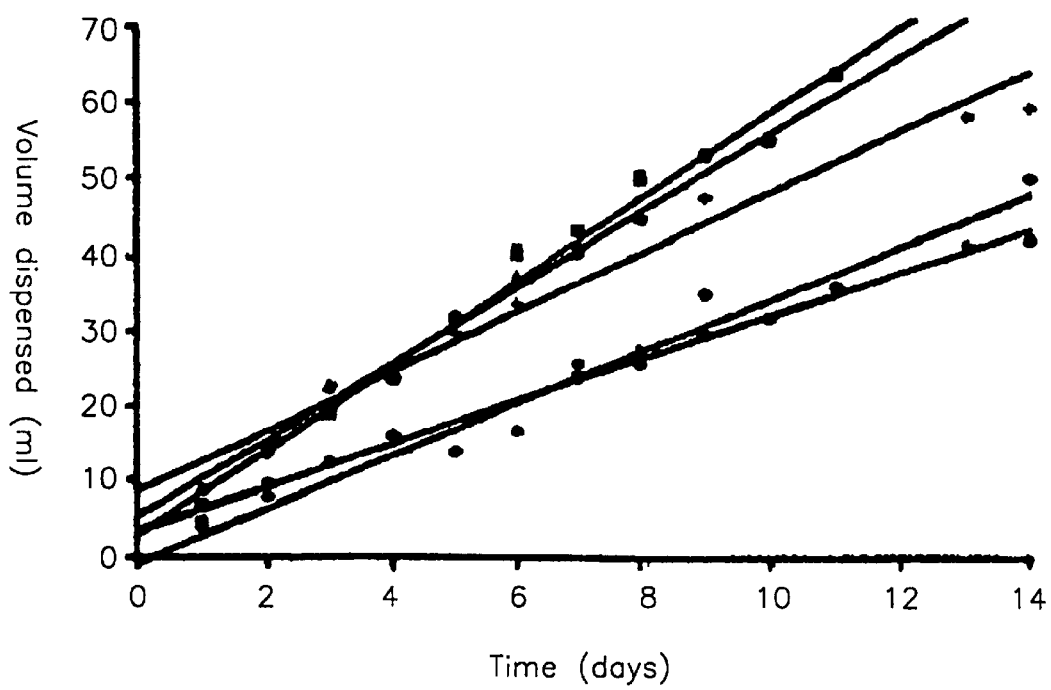
FIG. 28 shows an average volume of water dispensed from such a device as depicted in FIG. 23 against time for devices with different electrolytic cells agarose-dextrin (■), gelatin (▲), agarose-NaCl (●) and NaCl (♦) and NaHCO3 (+). Error bars are standard error means (n=3)

FIG. 28 shows an average volume of water dispensed from such a device as depicted in FIG. 23 against time for devices with different electrolytic cells agarose-dextrin, (■), gelatin (▲), agarose-NaCl (●) and NaCl (♦) and NaHCO3 (+). Error bars are standard error means (n=3).

Figure 29:
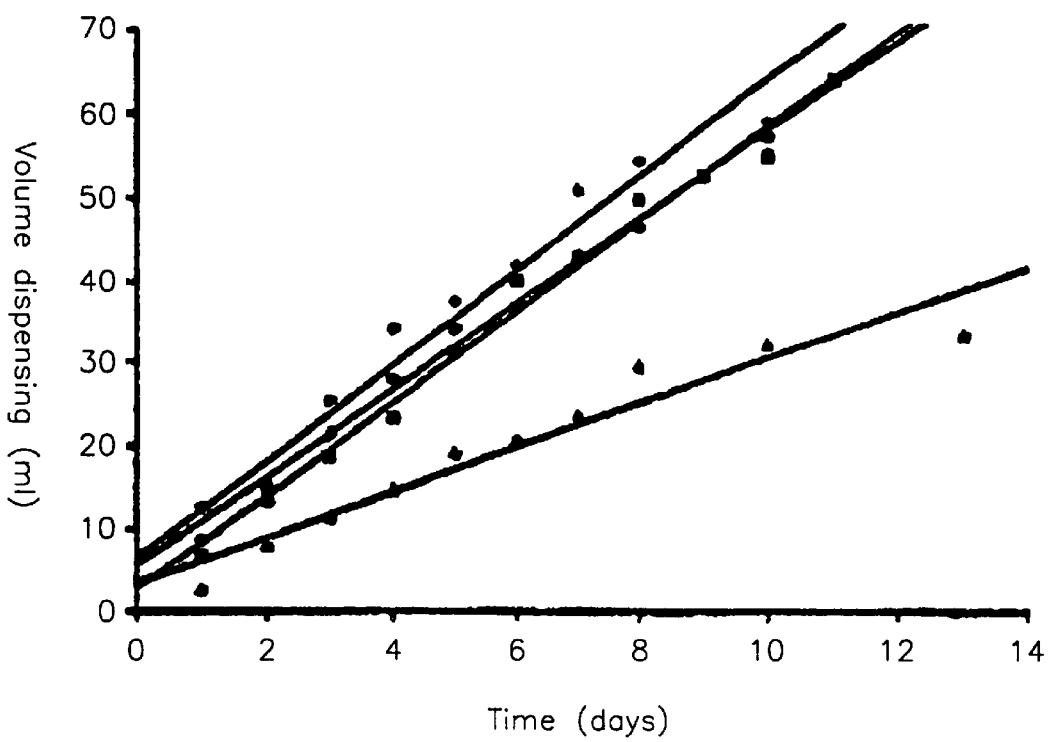
FIG. 29 shows an average volume of water dispensed from such a device as depicted in FIG. 23 against time for devices operated at different temperatures 4° C. (s), 25° C. and 16 cm (n), 38° C. (u) and 2 cm (1). Error bars are standard error means (n=3).

FIG. 29 shows an average volume of water dispensed from such a device as depicted in FIG. 23 against time for devices operated at different temperatures 4° C. (s), 25° C. and 16 cm (n), 38° C. (u) and 2 cm (1). Error bars are standard error means (n=3).

The release rate of vehicle from devices as depicted in FIG. 23 are summarized in the following table.

TABLE 7

Effect of outlet internal diameter, electrolytic current, electrolytic cell composition, depth and temperature on the zero-order release rate (r2 > 0.9700) of water from such a device as depicted in FIG. 23.

| Outinternal diameter (mm) | 1.10 | 0.18 | 0.25 | 0.51 | 1.02 |
|---|---|---|---|---|---|
| Dispensing rate ± sem (ml/day) | 3.28 ± 0.10 | 3.86 ± 0.85 | 5.81 ± 0.24 | 6.82 ± 0.51 | 6.87 ± 0.02 |
| Electrolytic current (mA) | 0.0 | 0.1 | 0.3 | 0.5 | |
| Dispensing rate ± sem (ml/day) | 0.14 ± 0.05 | 0.14 ± 0.05 | 2.92 ± 0.25 | 5.81 ± 0.24 | |
| Electrolytic cell composition | agarose-dextrim | agarose/NaCl | gelatin | NaCl | NaHCO3 |
| Dispensing rate | 5.81 ± 0.24 | 2.90 ± 0.13 | 5.08 ± 0.31 | 3.49 ± 0.07 | 3.98 ± 0.04 |
| Depth and temperature | 2 cm | 16 cm | 4° C. | 22° C. | 38° C. |
| Dispensing rate ± sem (ml/day) | 4.84 ± 0.39 | 5.81 ± 0.24 | 2.45 ± 0.41 | 5.81 ± 0.24 | 5.45 ± 0.44 |

A feature of the present invention is the simplicity of the delivery aspect within the retention body, its controllability and the prospect to improve the volume available from which active ingredient can be expressed. With the preferred embodiments the simplicity of the arrangements within the retention device ensures the prospect of locating the liquid sensitive components at an end of the device away from the liquids to be dispensed unlike the prior art devices discussed.

The continuous uninterrupted or pulsile dispensing ability of the devices of the present invention (depending upon what dispensing profile may be mandated in any particular application and the simplicity of construction is believed will find favour.

The devices of the present invention can also be programmed to investigate optimum blood serum levels (eg; progesterone et al) relevant (eg; to synchronisation) and that data then be used either to program devices for general sale or to be used with a view to matching passive devices to that desired outcome.

What is claimed is:

1. A delivery device having a reservoir of variable volume having an outlet through which an included vehicle can be expressed in liquid from as the volume of the reservoir is actively reduced and wherein there is a dip tube providing a conduit to the outlet from the reservoir of such length and crosssection as to favour active release over passive release.

2. The device of claim 1 wherein the dip tube is in part within a collapsible bladder.

3. The device of claim 1 wherein the dip tube is part of a cylinder to reduce the reservoir volume.

4. The device of claim 1 wherein said dip tube is a plastic tube of circular cross-section less than 1 mm in internal diameter.

5. The device of claim 1 wherein the dip tube is such that the passive vehicle release rate of the device is less than 50% of the initial volume of vehicle over any insertion period.

6. The device of claim 5 wherein said passive release rate is less than 20%.

7. The device of claim 1 wherein said outlet, at least prior to first use, is capped.

8. The device of claim 1 wherein said reservoir is reduced in volume continuously.

9. The device of claim 1 wherein said reservoir is reduced in volume intermittently.

10. The device of claim 1 wherein active reduction of the volume is under the action of either
   i) a gas or gases generated by the application of a controlled or controllable electric current to a water containing matrix at least one of contained, carried by and associated with the device in such a way as generates free oxygen and free hydrogen, or
   ii) a gas or gases generated by the electrolysis of water contained in a hydrogel, at least one of, contained and carried by the device.

11. The device of claim 10 wherein said vehicle is or contains progesterone.

12. The device of claim 11 which is an intra vaginal device and the rate of expression enabled, whilst in the vaginal tract of a target mammal, by the content of a bladder containing the vehicle, the outlet and the gas generating means is sufficient to first achieve a progesterone plasma level above 2 ng/mL and thereafter maintain a level of at least 2 ng/mL in the mammal for a period of at least 4 days.

13. The device of claim 12 wherein the vehicle content of the bladder is from 1 to 60 mL.

14. The device of claim 10 wherein said device includes a plurality of reservoirs of variable geometry each separately controlled insofar as the expression therefrom of its content is concerned.

15. The device of claim 10, wherein the free oxygen and free hydrogen generated is done in the absence of other gases.

16. The device of claim 10, wherein the hydrogel is negatively charged for enabling hydrolysis of the water.

17. The device of claim 1 wherein the active reduction is under the action of gas (es) generated by at least one of a timer and a microprocessor control of a supply of an electrolysing electric current to a hydrogel.

18. The device of claim 17 wherein the source of electric current is from a battery contained by, carried or associated with the device.

19. The device of claim 17 wherein there is sufficient hydrogel to enable an active delivery of greater than 80% of the initial vehicle volume in a recommended insertion period.

20. The device of claim 19 wherein the recommended insertion period is at least 4 days.

21. The device of claim 11 wherein said device has a removable seal or cap on said outlet and is at least one of (i) capable of being removed prior to intra vaginal insertion, (ii) dissolves in the vaginal tract after insertion and (iii) is rupturable under the pressure of the vehicle to be released after sufficient gas has been generated by said gas generating means after a switch energizes a circuit.

22. A delivery device capable of expressing a liquid vehicle from an outlet of a reservoir, said device having at least one of a timer and a microprocessor, a power source and circuitry, electrodes and electrolyte matrix to be able to generate a gas from the electrolyte matrix so as to reduce the volume of the reservoir to cause active expression of the vehicle therefrom, there being a dip tube providing a conduit to the outlet from the reservoir of such length and crosssection as to favour active release of the vehicle from the reservoir over passive release of the vehicle from the reservoir.

23. The device of claim 22 wherein the conduct by capillary or other resistance to passive flow of the vehicles from the reservoir is such as to reduce any passive eggress of the vehicle.

24. A delivery device capable of expressing a liquid vehicle from the outlet of a reservoir, said device having at least one of a timer and a microprocessor, a power source and circuitry, electrodes and electrolyte matrix to be able to generate a gas from the electrolyte matrix so as to reduce the volume of the reservoir to cause active expression of the vehicle therefrom, there being a dip tube providing a conduit to the outlet.

25. A delivery device having a body, wherein said body has
- a chamber having an outlet,
- a bladder within said chamber sealed about said outlet to said body so as to be capable of delivering its contents via said outlet upon the application of gas pressure external of said bladder to the bladder, said bladder containing at least 1 mL of progesterone in a liquid delivery form, a dip tube providing a conduit to the outlet from within the bladder to affect the passive leakage rate of the delivery device, and
- controlled or controllable gas generating means to generate a gas within said body so as to apply gas pressure within said chamber to the exterior of said bladder, and wherein the gas generating means include
- a hydrogel having electrolysis electrodes,
- a batter powered circuit capable of applying a controlled or set current to said electrolysis electrodes so as to generate gas from the hydrogel which will have a pressurising effect on the exterior of said bladder,
- switch means to allow energising of the circuit.

26. The device of claim 25 which is an intra vaginal device having an elongate body structure coupled to or having resilient means of variable geometry to facilitate in a target mammal vaginal tract insertion, to facilitate vaginal tract retention and to allow vaginal tract withdrawal, when the elongate axis of said body structure is substantially aligned to an axis of the vaginal tract.

27. The device of claim 25 wherein the rate of expression enabled, whilst in the vaginal tract of the target mammal, by the content of the bladder, the outlet and the gas generating means is sufficient to first achieve a progesterone plasma level above 2 ng/mL and thereafter maintain a level of at least 2 ng/mL in the mammal for a period of at least 4 days.

28. The device of claim 25 wherein said dip tub is a plastic tube of circular crosssection less than 1 mm in internal diameter.

* * * * *